US012636421B2

(12) United States Patent
Keating et al.

(10) Patent No.: US 12,636,421 B2
(45) Date of Patent: May 26, 2026

(54) CYCLIC ASPIRATION SYSTEM WITH A NON-POWERED INTERNAL STRUCTURAL IMPEDIMENT ENGAGING WITH A CLOT ASSISTING IN CAPTURE

(71) Applicant: Neuravi Limited, Galway (IE)

(72) Inventors: Karl Keating, Galway (IE); AnnaLisa Smullin, Galway (IE); Aoife Glynn, Galway (IE); Sarah Johnson, Galway (IE); David Quinn, Galway (IE); David Vale, Barna (IE); Patrick Griffin, Castlegar (IE); Tommy Gibbons, Galway (IE); Chris Brooks, Galway (IE); Patrick Brouwer, Galway (IE)

(73) Assignee: Neuravi Limited, Galway (IE)

( * ) Notice: Subject to any disclaimer, the term of this patent is extended or adjusted under 35 U.S.C. 154(b) by 149 days.

(21) Appl. No.: 18/441,030

(22) Filed: Feb. 14, 2024

(65) Prior Publication Data

US 2024/0277363 A1 Aug. 22, 2024

Related U.S. Application Data

(60) Provisional application No. 63/447,506, filed on Feb. 22, 2023.

(51) Int. Cl.
A61M 1/00 (2006.01)
A61B 17/00 (2006.01)
(Continued)

(52) U.S. Cl.
CPC ............... A61M 1/75 (2021.05); A61B 17/22 (2013.01); A61B 17/221 (2013.01); A61M 1/842 (2021.05);
(Continued)

(58) Field of Classification Search
CPC . A61B 17/22; A61B 17/22031; A61B 17/221; A61B 2017/00154;
(Continued)

(56) References Cited

U.S. PATENT DOCUMENTS

2002/0198550 A1 12/2002 Nash et al.
2004/0019310 A1 1/2004 Hogendijik
(Continued)

FOREIGN PATENT DOCUMENTS

WO 2014151209 A1 9/2014

*Primary Examiner* — Kankindi Rwego
(74) *Attorney, Agent, or Firm* — Troutman Pepper Locke LLP

(57) ABSTRACT

Cyclic aspiration system including an aspiration catheter and a cyclic aspiration source connected in fluid communication thereto, wherein the cyclic aspiration pressure source produces a cyclic aspiration pressure waveform of intermittently cycling intervals of a vacuum pressure below atmospheric pressure and a positive pressure higher than the vacuum pressure. The system further including a non-powered internal structural impediment disposed within the lumen of the aspiration catheter and configured to engage with a clot capturable therein during resulting movement between the clot and the non-powered internal structural impediment while subject to the cyclic aspiration pressure waveform to assist in capture of the clot. The non-powered internal structural impediment may be permanently attached to the aspiration catheter or a separate component or device independently slidable within the lumen of the aspiration catheter.

20 Claims, 19 Drawing Sheets

(51) Int. Cl.

| | |
|---|---|
| *A61B 17/22* | (2006.01) |
| *A61B 17/221* | (2006.01) |
| *A61M 25/00* | (2006.01) |
| *A61M 25/01* | (2006.01) |
| *A61M 25/10* | (2013.01) |

(52) U.S. Cl.
CPC ............... *A61B 2017/00022* (2013.01); *A61B 2017/00154* (2013.01); *A61B 2017/00172* (2013.01); *A61B 2017/0023* (2013.01); *A61B 2017/00292* (2013.01); *A61B 2017/00367* (2013.01); *A61B 2017/00398* (2013.01); *A61B 2017/00544* (2013.01); *A61B 2017/00561* (2013.01); *A61B 2017/00862* (2013.01); *A61B 2017/00867* (2013.01); *A61B 2017/22067* (2013.01); *A61B 2017/22079* (2013.01); *A61B 2017/2212* (2013.01); *A61B 2017/2215* (2013.01); *A61B 2217/005* (2013.01); *A61M 2025/0002* (2013.01); *A61M 2025/0004* (2013.01); *A61M 25/003* (2013.01); *A61M 2025/0031* (2013.01); *A61M 2025/0039* (2013.01); *A61M 2025/0059* (2013.01); *A61M 25/0068* (2013.01); *A61M 25/0074* (2013.01); *A61M 25/0158* (2013.01); *A61M 2025/1052* (2013.01); *A61M 2205/3327* (2013.01); *A61M 2205/3351* (2013.01)

(58) Field of Classification Search
CPC ........... A61B 2017/00172; A61B 2017/00561; A61B 2017/00566; A61B 2017/22034; A61B 2017/22035; A61B 2017/2212; A61B 2017/2215; A61B 2017/2217; A61B 2217/005; A61M 25/003; A61M 25/0067; A61M 25/0074; A61M 2205/3351

USPC .......................................... 606/127, 159, 200
See application file for complete search history.

(56) References Cited

U.S. PATENT DOCUMENTS

| | | | |
|---|---|---|---|
| 2011/0034986 A1 | 2/2011 | Chou et al. | |
| 2016/0135829 A1* | 5/2016 | Holochwost | A61B 17/22 |
| | | | 606/159 |
| 2019/0239910 A1* | 8/2019 | Brady | A61B 17/22012 |
| 2020/0129751 A1 | 4/2020 | Malkowski et al. | |

* cited by examiner

650

605

650

605

BLOOD FLOW

805

850

850

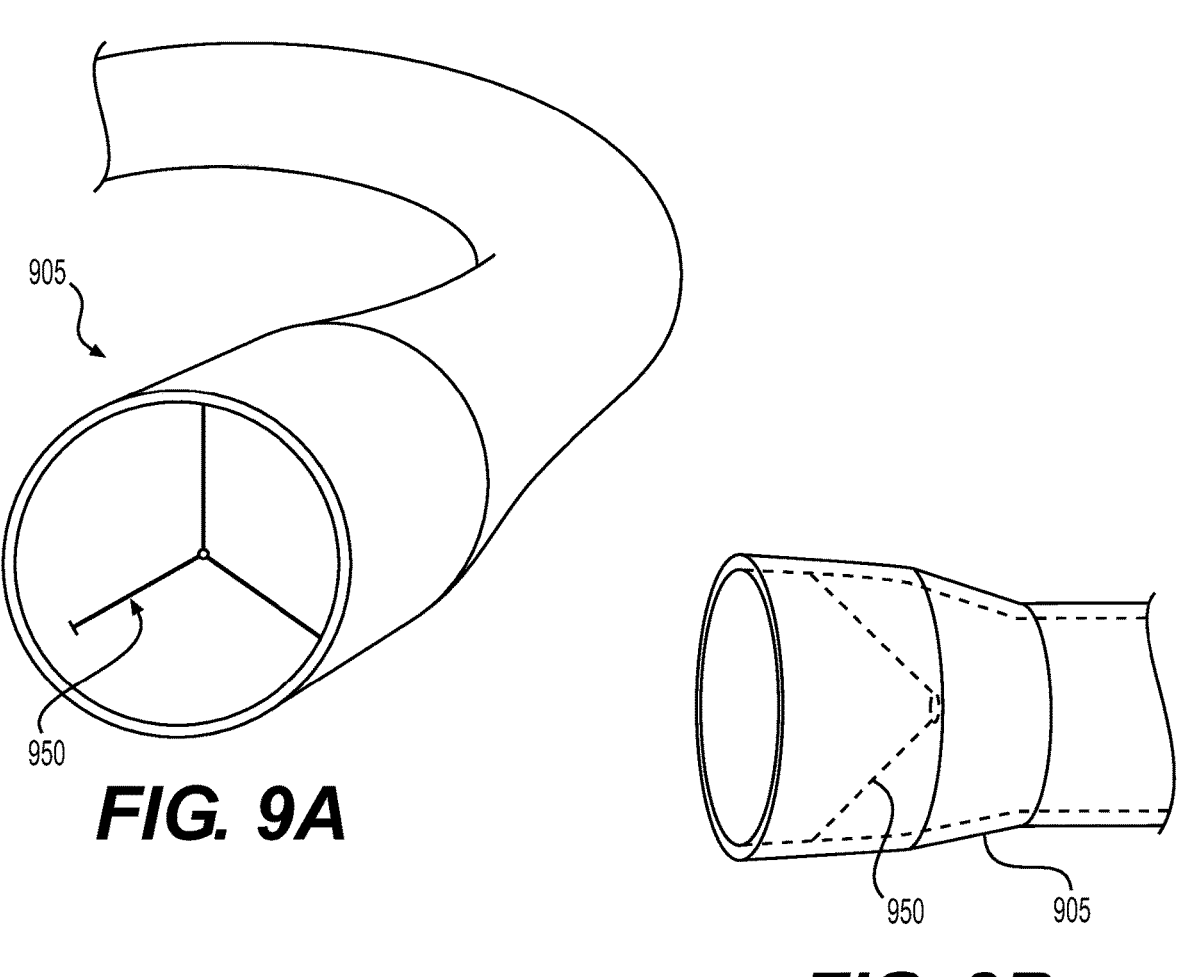
905
950
FIG. 9A
950          905
FIG. 9B
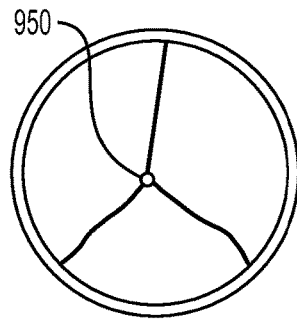
950
FIG. 9C
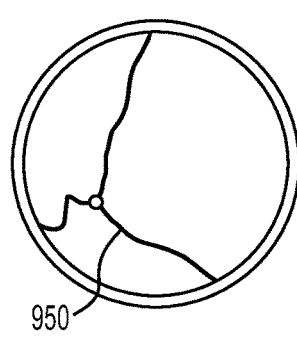
950
FIG. 9D
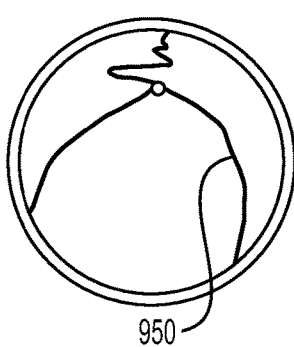
950
FIG. 9E

CYCLIC ASPIRATION SYSTEM WITH A NON-POWERED INTERNAL STRUCTURAL IMPEDIMENT ENGAGING WITH A CLOT ASSISTING IN CAPTURE

CROSS-REFERENCE TO RELATED APPLICATION

This application claims the benefit of U.S. Provisional Patent Application No. 63/447,506, filed on Feb. 22, 2023, the disclosure of which is incorporated herein by reference in its entirety.

FIELD

The present disclosure generally relates to an aspiration system for use during a thrombectomy procedure to capture and remove a targeted clot. Preferably the present disclosure relates to a cyclic aspiration system that assists or aids in capture of a clot, particularly, fibrin rich clots and/or clots so large in size as not able to be received in conventional aspiration catheters, by the clot engaging with a non-powered internal structural impediment.

BACKGROUND

During endovascular treatment, the targeted clot is often a fibrin rich clot of densely compacted fibrin threads entangling platelets to form a hardened mass hampering ingestion into the catheter via aspiration. Another factor impacting successful ingestion of the clot into the catheter via aspiration is if the overall size of the occlusion is so large as to be unable to be accommodated within the aspiration catheter. These characteristics pose significant challenges in the effective capture and removal of the targeted clot via aspiration catheters. It is therefore desirable to develop an improved cyclic aspiration system that address these concerns by including an internal structural impediment configured to engage with a clot and assist in capture.

SUMMARY

An aspect of the present disclosure is directed to an improved cyclic aspiration system particularly for use with capturing fibrin rich clots or clots whose overall size is so large as to be unable to be accommodated within the aspiration catheter.

A further aspect of the present disclosure is directed to an improved cyclic aspiration system with greater efficiency in capture/ingestion and removal of the clot in the aspiration catheter by physically altering its state while being ingested.

While a still further aspect of the present disclosure is directed to an improved cyclic aspiration system including a non-powered internal structural impediment disposed in the lumen of the aspiration catheter engaging with the clot and assisting in capture by leveraging kinetic energy during cyclic aspiration so that the internal structural impediment does not require its own power source (i.e., non-powered). Simplifying and minimizing the number of components of the non-powered internal structural impediment in this manner, minimizes the bulkiness, footprint, weight, and expense of the cyclic aspiration system in accordance with the present disclosure.

BRIEF DESCRIPTION OF THE DRAWINGS

The above and further aspects of the present disclosure are further discussed with reference to the following description in conjunction with the accompanying drawings, in which like numerals indicate like structural elements and features in various figures. The drawings are not necessarily to scale, emphasis instead being placed upon illustrating principles of the present disclosure. The figures depict one or more implementations of the devices, by way of example only, not by way of limitation.

FIG. 9A is a perspective view of a distal section of still another example aspiration catheter including a multi-segment fiber acting as the non-powered internal structural impediment in accordance with the present disclosure, the multi-segment fiber having sufficient slack to be displaceable and reconfigurable while remaining secured within the lumen of the aspiration catheter;

FIG. 9B is a side view of the distal section of the aspiration catheter of FIG. 9A;

FIGS. 9C-9E depict a distal end of the aspiration catheter of FIG. 9A with the multi-segment fiber displaced in several illustrative exemplary reconfigurations to accommodate passage of an auxiliary device therethrough without interfering with the multi-segment fiber;

DETAILED DESCRIPTION

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±20% of the recited value, e.g. "about 90%" may refer to the range of values from 71% to 99%.

As used herein, the terms "tubular" and "tube" are to be construed broadly and are not limited to a structure that is a right cylinder or strictly circumferential in cross-section or of a uniform cross-section throughout its length. For example, a tubular structure or system is generally illustrated as a substantially right cylindrical structure. However, the tubular system may have a tapered or curved outer surface without departing from the scope of the present disclosure.

Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

Conventional aspiration catheters are prone to clogging when used to capture fibrin rich clots and/or oversized clots exceeding in overall size that of the aspiration catheter. It is therefore desirable to develop an improved aspiration catheter having a non-powered (i.e., does not require its own energy or power source, e.g., battery or other electrical power supply) internal structural impediment for severing, cutting up, tearing apart, restraining, and/or altering in shape the clot thereby improving efficiency of its capture/ingestion therein and removal. Rather than having to power the internal structural impediment, instead the kinetic energy imparted while applying cyclic or pulsatile aspiration is leveraged resulting in movement between the clot and the non-powered internal structural impediment (e.g., movement of the clot while the internal structural impediment remains stationary or movement of the internal structural impediment while the clot remains stationary).

Figure 12:
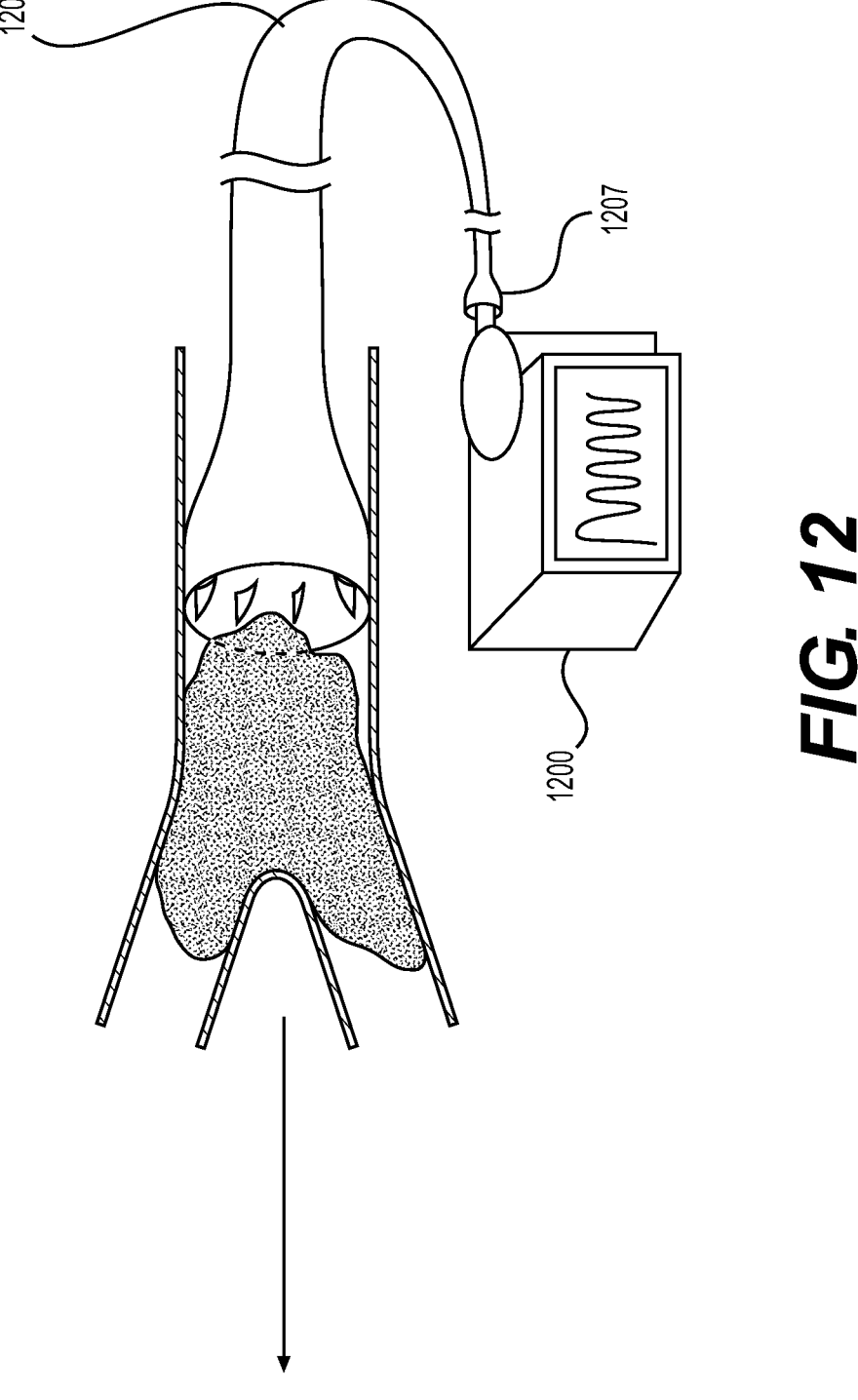
FIG. 12 is an example aspiration catheter system including a pulsatile vacuum pump connected in fluid communication to an aspiration catheter delivered to a target site prior to capturing/ingesting a clot therein, wherein any of the example non-powered internal structural impediments illustrated above may be disposed within the lumen of the aspiration catheter thereof.

A system and method in accordance with the present disclosure is directed to an improved cyclic aspiration system for the capture and removal of a clot. An example cyclic aspiration system is depicted in FIG. 12 including a cyclic aspiration source (e.g., a pulsatile vacuum pump) 1200 connected to a proximal hub 1207 on a proximal end of an aspiration catheter 1205. The aspiration catheter 1205 has disposed in a distal section of the lumen proximally of the distal tip/end an internal structural impediment in accordance with any one of the examples illustrated herein and described in detail below. The cyclic aspiration source produces a cyclic aspiration pressure waveform of intermittent cyclic intervals of vacuum pressure below atmospheric pressure and positive pressure higher than the vacuum pressure, possibly higher than atmospheric pressure. FIG. 12 illustrates the aspiration catheter being delivered through the vessel to the target site of a clot prior to applying cyclic aspiration. The kinetic energy while subject to cyclic aspiration is leveraged resulting in engagement between the clot and the non-powered internal structural impediment. In accordance with the present disclosure, engagement of the clot with the non-powered internal structural impediment results in: (i) disrupting the structure of the clot from that of a single unitary mass severed, divided, cut up, or torn apart into two or more clot pieces; (ii) altering the shape of at least a portion of the clot (e.g., reconfiguring, reshaping, and/or elongating); and/or (iii) restricting distal movement of the clot capturable therein. With some of the example non-powered internal structural impediments, may retain, grip, clamp, or hold a portion of the captured clot within the aspiration catheter restricting the distal movement of the clot while minimizing risk of expulsion of the clot from the distal end. While in some instances, during the positive pressure interval of cyclic aspiration, the non-powered internal structural impediment may alter in shape (e.g., elongate) the clot thereby improving capture/ingestion. Engagement of the clot and the non-powered internal structural impediment in accordance with the present disclosure improves the efficiency of capture/ingestion while minimizing the risk of the clot becoming clogged in the aspiration catheter.

Non-limiting examples of the non-powered internal structural impediment member in accordance with the present disclosure are illustrated and described herein but others are contemplated. In some examples the non-powered internal structural impediment is permanently secured in place within the lumen of the aspiration catheter itself, while in other examples the non-powered internal structural impediment is a separate component or device independently slidable within the lumen of the aspiration catheter.

Figure 1A:
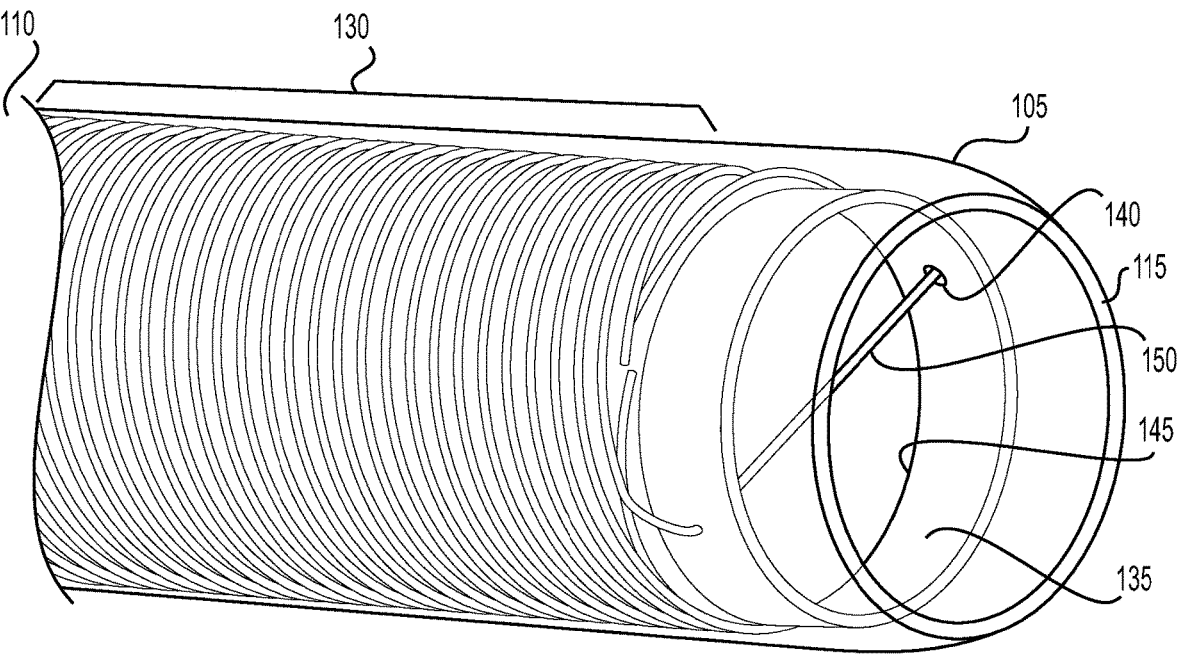
FIG. 1A is a perspective view of a distal section of an example aspiration catheter with a single taut wire spanning at least a portion of the lumen thereof acting as the non-powered internal structural impediment in accordance with the present disclosure.
Figure 1B:
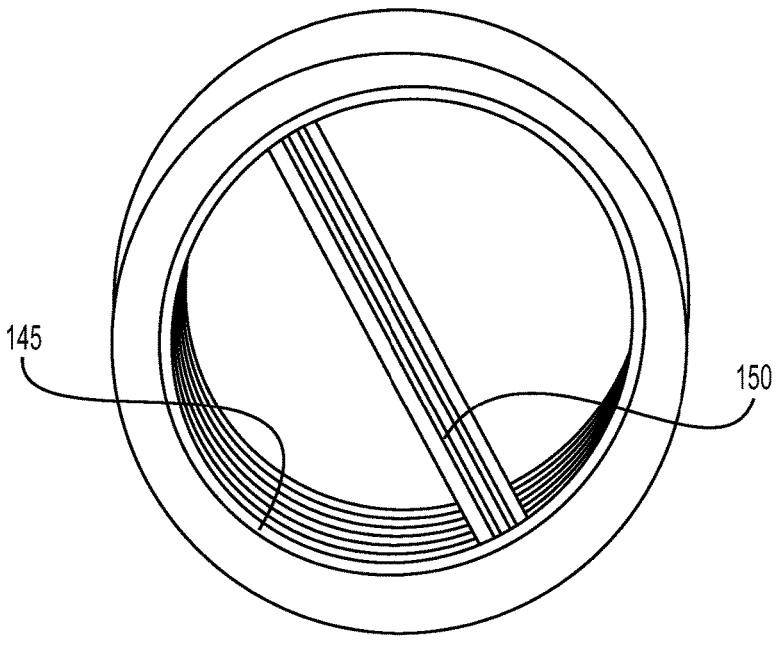
FIG. 1B is a distal end view of the aspiration catheter of FIG. 1A.
Figure 1C:
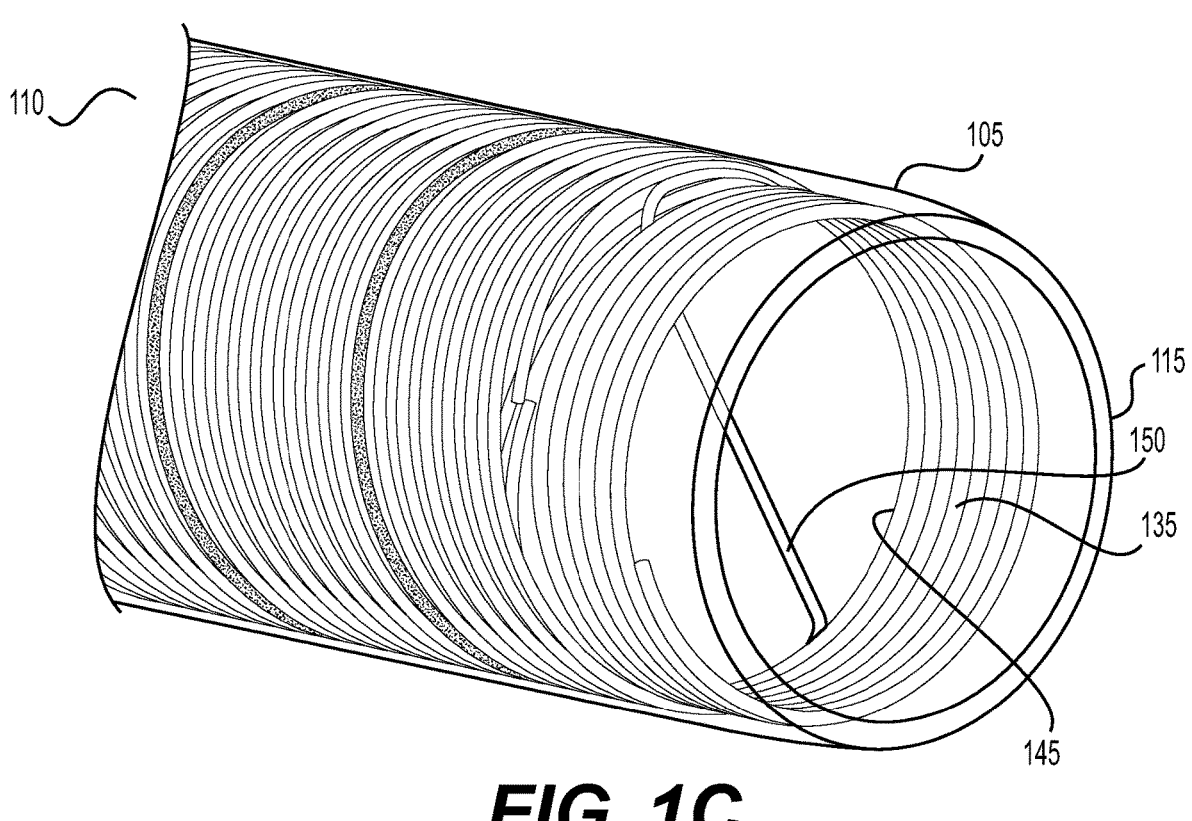
FIG. 1C is a perspective view of the distal section of a modified example aspiration catheter of FIG. 1A with a single taut wire spanning at least a portion of the lumen thereof acting as the non-powered internal structural impediment in accordance with the present disclosure, wherein the taut wire is secured to a proximal braid section and extends distally thereof forming a distal coil section.
Figure 1D:
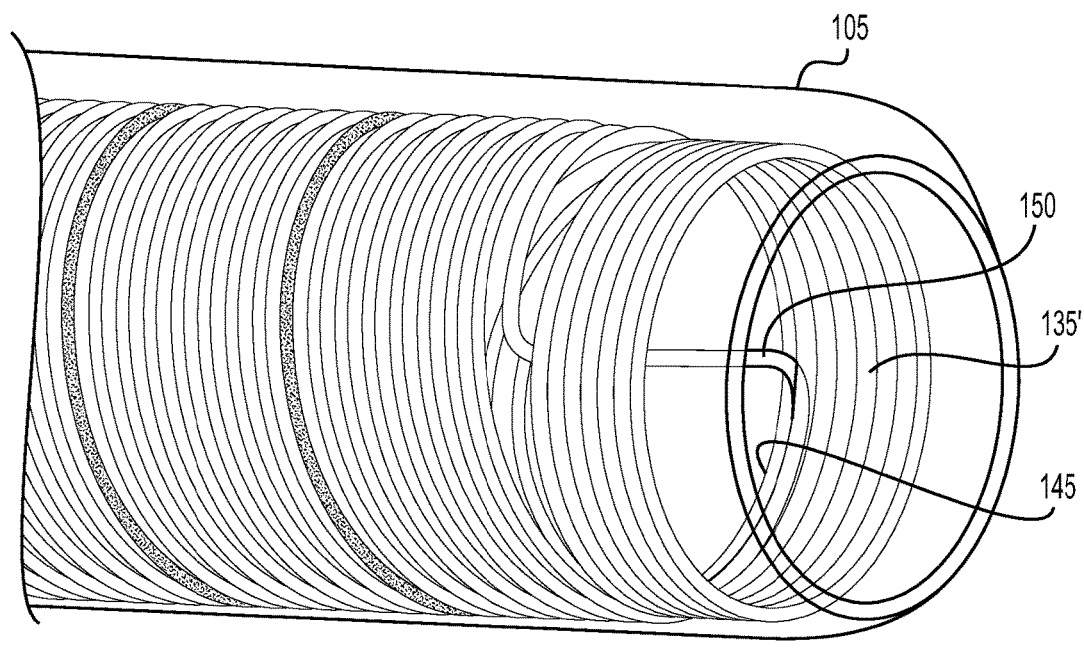
FIG. 1D is a side view of the aspiration catheter of FIG. 1C.

The examples described first are of the non-powered internal structural impediment permanently secured in place within the lumen of the aspiration catheter itself. In FIGS. 1A & 1B, the cyclic aspiration system includes an aspiration catheter 105. As depicted in the perspective view of the distal section of the aspiration catheter 105 having a distal end 115 in FIG. 1A, secured within the lumen of the aspiration catheter 105 is a braided proximal section 130 and a marker band section 135 disposed distally thereof having an opening 145. In the example in FIGS. 1A & 1B, the internal structural impediment is a taut wire 150 extending or spanning at least a portion of the lumen of the aspiration catheter 105. The distal end view in FIG. 1B depicts the example wire 150 spanning the full diameter of the opening 145 (i.e., approximately the full diameter of the lumen of the aspiration catheter 105), but the wire 150 may alternative span only a segment or portion of the opening 145 (i.e., only a portion of the lumen of the aspiration catheter 105). In FIG. 1A, the wire 150 is integral with and extends from the braided proximal section 130, passes through a first opening (e.g., hole) 140 defined in the marker band section 135, across at least a section of the opening 145 of the marker band section 135, through a second opening (e.g., hole) 140 defined in the maker band section 135 where its opposite end is secured thereto (e.g., adhered, welded or otherwise permanently affixed). In an alternative arrangement, the wire 150 is integral with and extends from the braided proximal section 130, across at least a section of the opening 145, thereafter the wire 150 may be formed into a coil distal section 135' disposed distally of the braided proximal section 130 (FIGS. 1C & 1D). If the wire 150 is made of a radiopaque material (e.g., Tungsten) the coil distal section 135' may simultaneously serve as the marker band section. Alternative ways may be used to secure (e.g., adhere or weld) respective ends of the wire 150. Use of a single wire 150 as the internal structural impediment advantageously leaves sufficient free space for an auxiliary device(s) (e.g., guidewire, microcatheter, etc.) to be advanced through the lumen of the aspiration catheter without interfering with the wire 150.

Selection of the position of the wire 150 in an axial direction relative to the distal tip/end of the aspiration catheter 105 impacts the size of the pieces into which the clot is severed, divided, cut up, or torn apart during engagement resulting from back-and-forth (i.e., bi-directional) relative movement between the clot and the wire 150 while subject to cyclic aspiration. That is, placement of the wire 150 more proximally (i.e., further away from the distal tip/end 115 of the aspiration catheter 105) severs, divides, cuts up, or tears apart the clot into larger size pieces, while placement of the wire 150 more distally (i.e., closer towards the distal tip/end 115 of the aspiration catheter 105) sever, divides, cuts up, or tears apart the clot into smaller size pieces. In the example depicted in FIGS. 1A-1D the internal structural impediment is a single wire 150, however, more than one wire is contemplated and within the scope of the present disclosure. Multiple wires may be displaced at different locations along an axial/longitudinal length of the aspiration catheter 105 and/or multiple wires may be used at the same axial/longitudinal location (i.e., in the same radial plane) in the aspiration catheter 105 but extend along different paths traversing at least a portion of the lumen of the aspiration catheter 105.

Figure 1E:
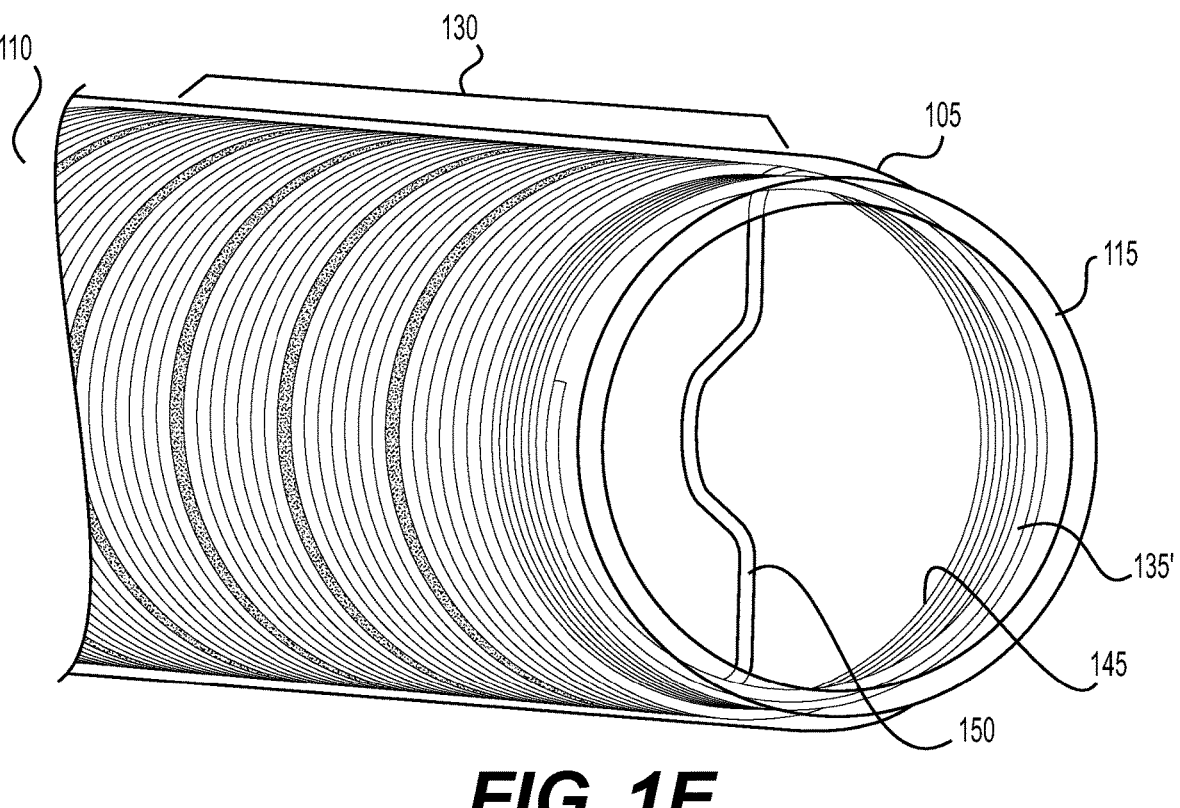
FIG. 1E is a side view of a distal section of still another example aspiration catheter having a single loose (i.e., not taut) wire spanning at least a portion of the lumen acting as the non-powered internal structural impediment in accordance with the present disclosure.
Figure 1F:
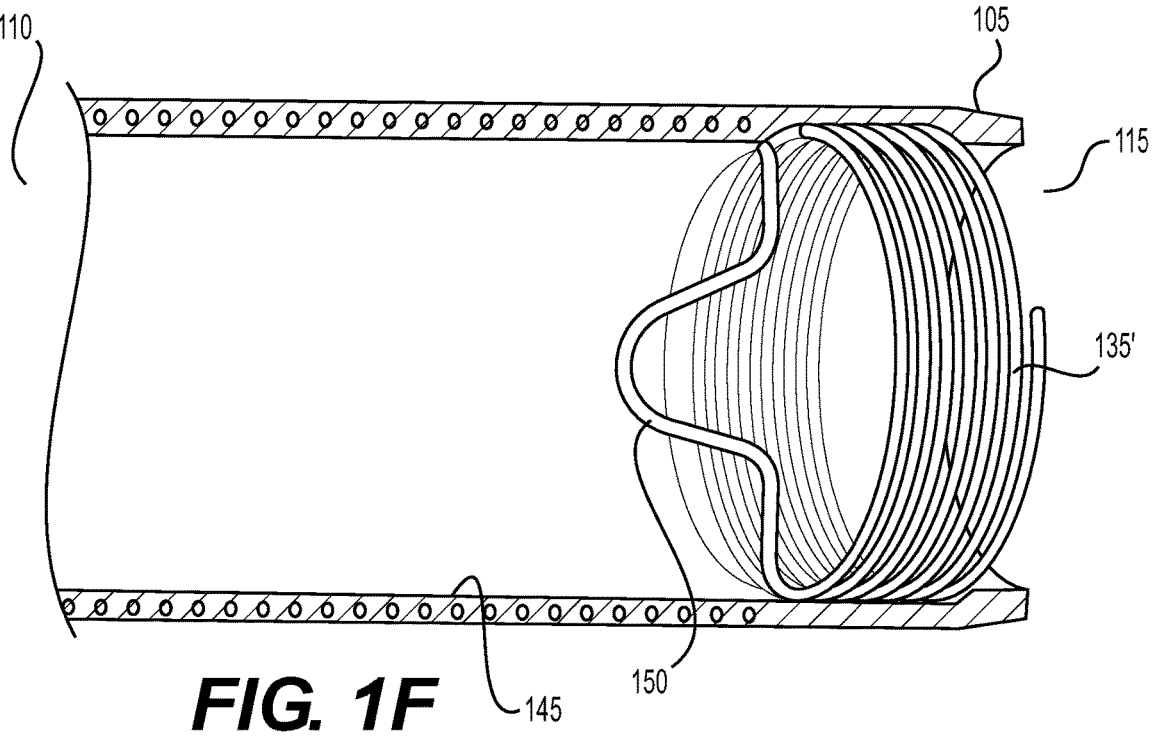
FIG. 1F is a side view of the aspiration catheter of FIG. 1E, wherein the aspiration catheter and proximal braid section are cut away to show the single loose wire spanning at least a portion of the lumen and forming the distal coil section.

The single wire 150 in FIGS. 1A-1D is tautly secured when spanning at least a portion of the opening 145 (i.e., at least a portion of the lumen of the aspiration catheter 105), however, the wire may otherwise be loose (i.e., not taut) resembling that of a string more than a wire, as illustrated in FIGS. 1E & 1F. By way of example, the loose wire 150 in FIGS. 1E & 1F has a single slack section (e.g., U-shape) but the number of discrete slack sections of the wire and shape thereof may be selected, as desired. After traversing the lumen, the loose wire 150 forms a coil distal section 135' of the internal sleeve 125 distally of a braided proximal section 130. The one or more slack sections of the wire 150 advantageously allow some movement or displacement out of the way permitting the passage of other auxiliary device(s) (e.g., guide wires, microcatheters, etc.) there-through the aspiration catheter without interference. More-over, those one or more slack sections of the wire 150 themselves move when subject to cyclic aspiration thereby further promoting severing, dividing, or tearing apart the clot into a plurality of pieces.

FIGS. 9A-9E depict still another example of the aspira-tion catheter 905 in accordance with the present disclosure wherein the internal structural impediment is a multi-seg-ment fiber (e.g., 3-segment fiber) 950. Each segment of the fiber is secured at a first end to an inner wall of the aspiration catheter 905 while an opposite second end is secured to one another in the lumen of the aspiration catheter 905 allowing for intentional reconfiguration or displacement of the multi-segment fiber 950. In the example illustrated, those first ends at which all three segments of fiber hare secured to one another are in a first radial plane arranged proximally relative to those opposite second ends permanently attached to the inner wall of the aspiration catheter 905 in a second radial plane (see the side view in FIG. 9B). FIGS. 9C-9E depict several illustrative examples of different reconfigu-rations of the multi-segment fiber 950 to allow passage of an auxiliary device(s) (e.g., guidewire, microcatheter, etc.) therethrough the lumen of the aspiration catheter 905 with-out interfering with the 3-segment fiber 950. Preferably, the fiber 950 is made of a material selected taking into consid-eration minimize profile and maximize strength sufficient to sever, divide, cut, or tear the clot into a plurality of pieces while engaging therewith during relative movement between the clot and non-powered internal structural impediment during aspiration.

Figures 1G, 1H:
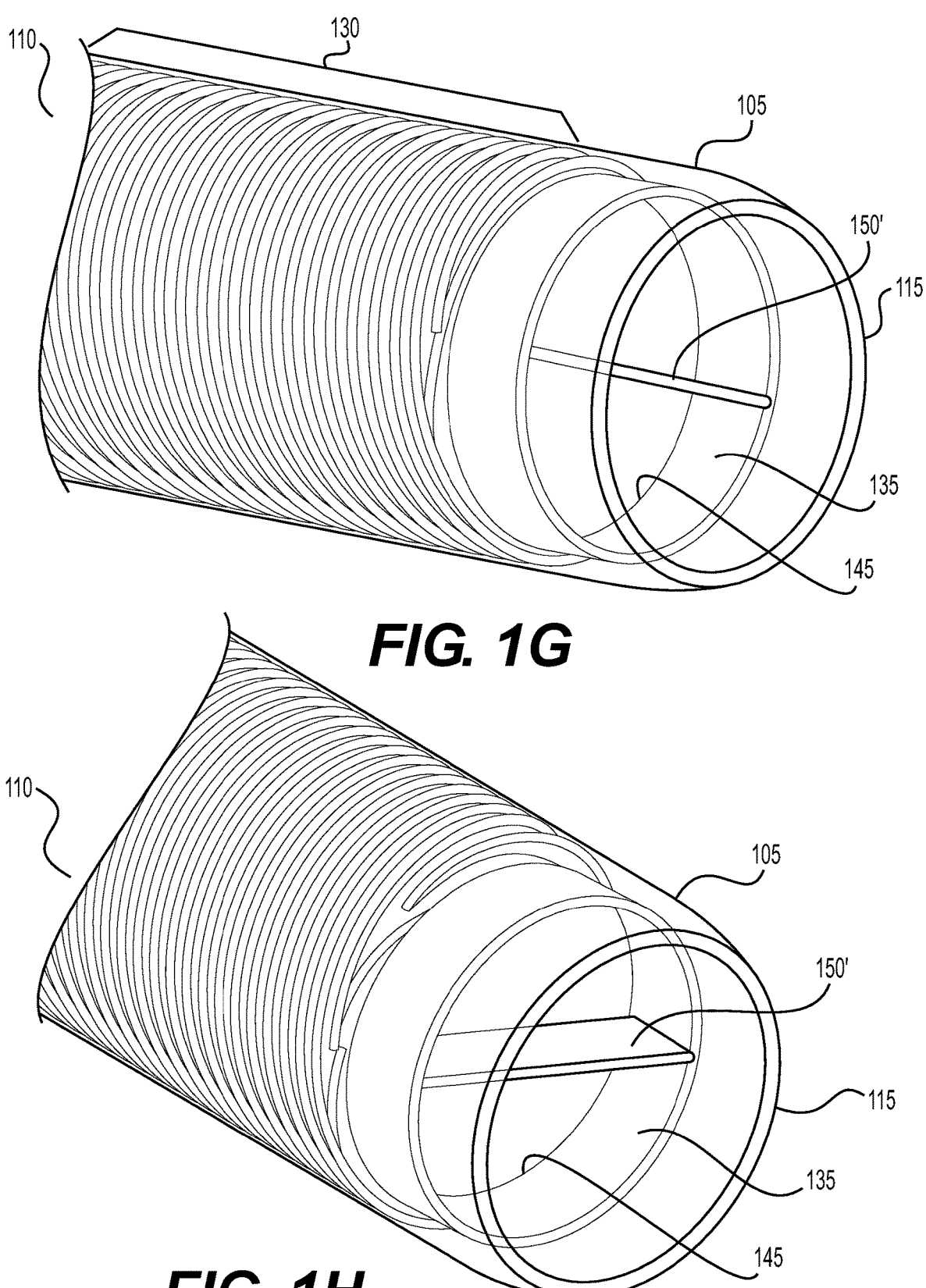
FIG. 1G is a perspective view of a distal section of yet another example aspiration catheter having a single rib (i.e., planar or straight) acting as the non-powered internal structural impediment in accordance with the present disclosure, wherein the single rib spans the lumen with its respective ends secured to the marker band section.
FIG. 1H is a perspective downward view of the aspiration catheter of FIG. 1G showing the single rib from another angle.

As an alternative to the aforementioned single, multiple, or multi-segment wire or fiber, the non-powered internal structural impediment spanning at least a portion of the opening 145 (i.e., at least a portion of the lumen of the aspiration catheter) may be a straight or linear rib (e.g., blade) 150'. FIGS. 1G & 1H depict an exemplary straight (i.e., planar or flat) rib 150' spanning the full diameter of the opening 145 (i.e., approximately the full diameter of the lumen of the aspiration catheter). Respective ends of the rib 150' are secured to an inner wall of the marker band section 135 arranged distally of the braided proximal section 130. To assist in severing, dividing, cutting up, or tearing apart the clot a distal edge of the rib may optionally be sharp (acting as a blade or knife) aiding in "cutting up" the clot during back-and-forth bi-directional movement between the clot and the rib 150' when under cyclic aspiration. However, even a rib 150' having a blunt distal edge will nevertheless sever, divide, cut up, or tear apart the clot, albeit less effectively than if sharp, when combined with cyclic aspi-ration.

In operation, all of the different examples described above with respect to FIGS. 1A-1H & 9A-9E act similarly in that, during cyclic aspiration, with each pass (i.e., back and forth) traversing the internal structural impediment (e.g., one or more wires, fibers or ribs) the clot is severed, divided, cut up, or torn apart. Specifically, during the vacuum pressure interval, the clot traverses the internal structural impediment (e.g., one or more wires, fibers, or ribs) in a proximal direction from a distal side to the proximal side. Whereas, during the positive pressure interval the clot traverses the internal structural impediment in the distal direction from the proximal side to the distal side. During relative move-ment between the clot and the non-powered internal struc-tural impediment in response to the cyclic aspiration pres-sure waveform the clot is severed, divided, cut up, or torn apart.

Figure 2:
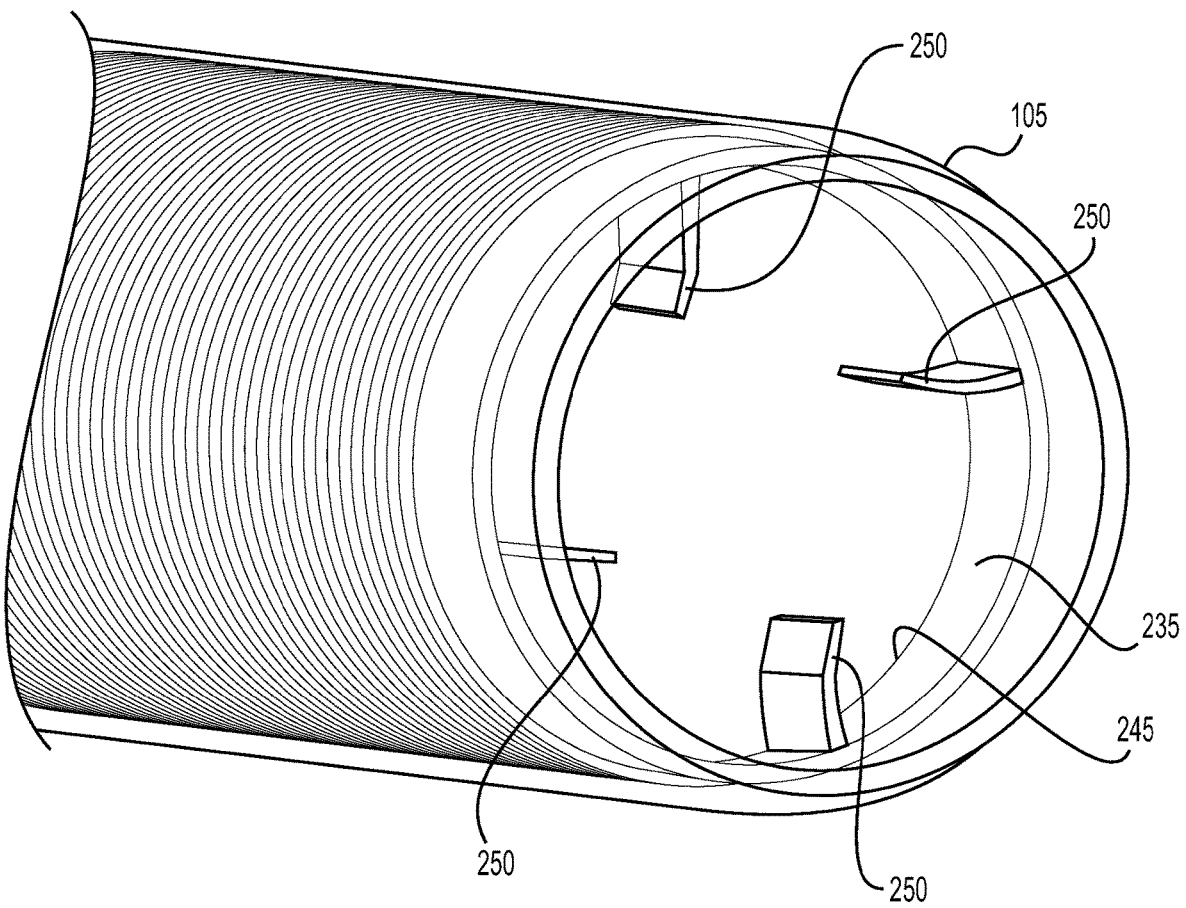
FIG. 2 is a perspective distal section view of still another example aspiration catheter having four radial ribs acting as the non-powered internal structural impediment in accordance with the present disclosure.

In those previously described examples of the wire, fiber, or rib as the non-powered internal structural impediment each respective end is attached to another component (e.g., to an inner wall of the marker band section, directly to the inner wall of the aspiration catheter, or to one another in the case of the 3-segment fiber). However, in accordance with the present disclosure it is possible for only one end of the internal structural impediment to be attached secured, while the opposite end remains free (i.e., not attached to any other component). One example of such configuration is an inter-nal structural impediment including one or more radial fins 250, with each fin 250 secured to the inner wall of the marker band 235 only at one end while its opposite second end is free projecting into the lumen of the aspiration catheter perpendicular to the inner wall. FIG. 2 diagram-matically depicts an internal structural member including four radially equidistantly arranged radial fins 250 but any number of one or more fins are contemplated and the arrangement of which along the inner wall of the maker band 235 need not necessarily be equidistant from one another. When cyclic aspiration is applied the radial fins 250 may create an aspiration vortex proximate the distal tip/end of the aspiration catheter that further assists in severing, macerat-ing, or tearing apart the clot. Preferably, the radial fins 250 are all curved in the same direction (e.g., clockwise or counterclockwise). During cyclic aspiration, the aspiration vortex generated in combination with the induced movement of clot relative to the radial fins fosters breaking up or tearing apart the clot.

Figure 3A:
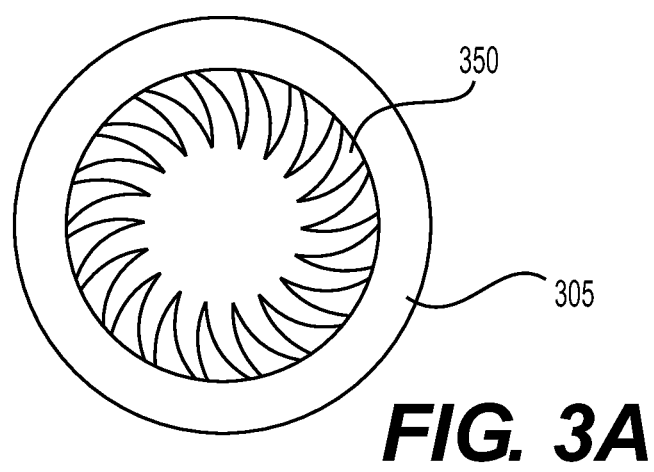
FIG. 3A is a distal end view of yet another example aspiration catheter including a ring of spiral teeth arranged 360 degrees acting as the non-powered internal structural impediment in accordance with the present disclosure.
Figure 3B:
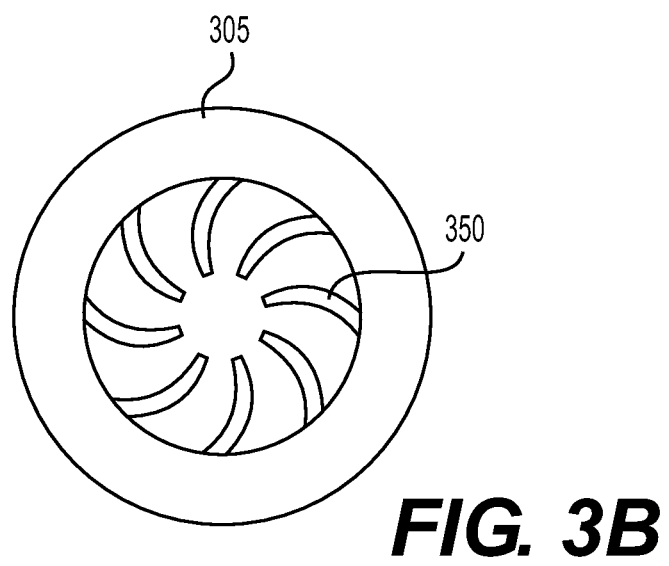
FIG. 3B is a distal end view of still yet another example aspiration catheter including a ring of spiral blades arranged 360 degrees acting as the non-powered internal structural impediment in accordance with the present disclosure.
Figure 3C:
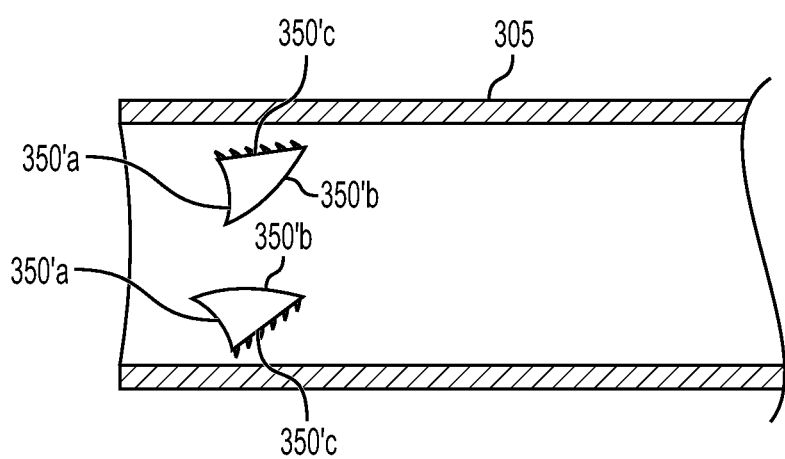
FIG. 3C is an axial cross-sectional cutaway view of a distal section of the example aspiration catheter of FIG. 3B depicting only two of the spiral blades to illustrate the shape and arrangement of the individual blades along an inner wall of the distal section of the aspiration catheter.

The radial cutting elements may be arranged as a ring of spiral teeth secured to the inner wall of the lumen of the aspiration catheter. FIG. 3A shows a distal end of a ring of spiral teeth 350 disposed within the lumen of the aspiration catheter. Each spiral tooth is secured at one end along an inner surface of the aspiration catheter while its opposite free end projects radially inward assists with macerating, severing, or tearing up the clot during engagement therewith while under cyclic aspiration. In an alternative configuration in FIG. 3B the non-powered internal structural impediment is a ring of spiral blades 350', with each blade 350' attached at one end 350'c to the inner wall of the aspiration catheter 305 while the free tip projects into the lumen. The spiral blades 350' are preferably deflectable or deformable when engaging with either: (i) the clot while under vacuum pressure; or (ii) an auxiliary device (e.g., internal catheter) during advancement in the distal direction through the lumen of the aspiration catheter. To foster deflection or deformation during engagement with the clot or auxiliary device, each blade 350' preferably has a distal facing edge 350'a projecting inwardly more than an opposite proximal facing edge 350'b, as shown in FIG. 3C. On the distal side, when subject to vacuum pressure, the clot while moving in the proximal direction engages (i.e., catches) on the distal facing edges 350'a lifting or raising the blades away from the inner wall of the aspiration catheter thereby increasing engagement therewith. Whereas on the proximal side, an auxiliary device (e.g., inner catheter) while advanced in the distal direction through the lumen of the aspiration catheter engages with (i.e., brushes over) the proximal facing edges 350'b collapsing, pushing, deforming the blades towards the inner wall of the aspiration catheter thereby allowing passage therethrough.

Figures 4A, 4B, 4C:
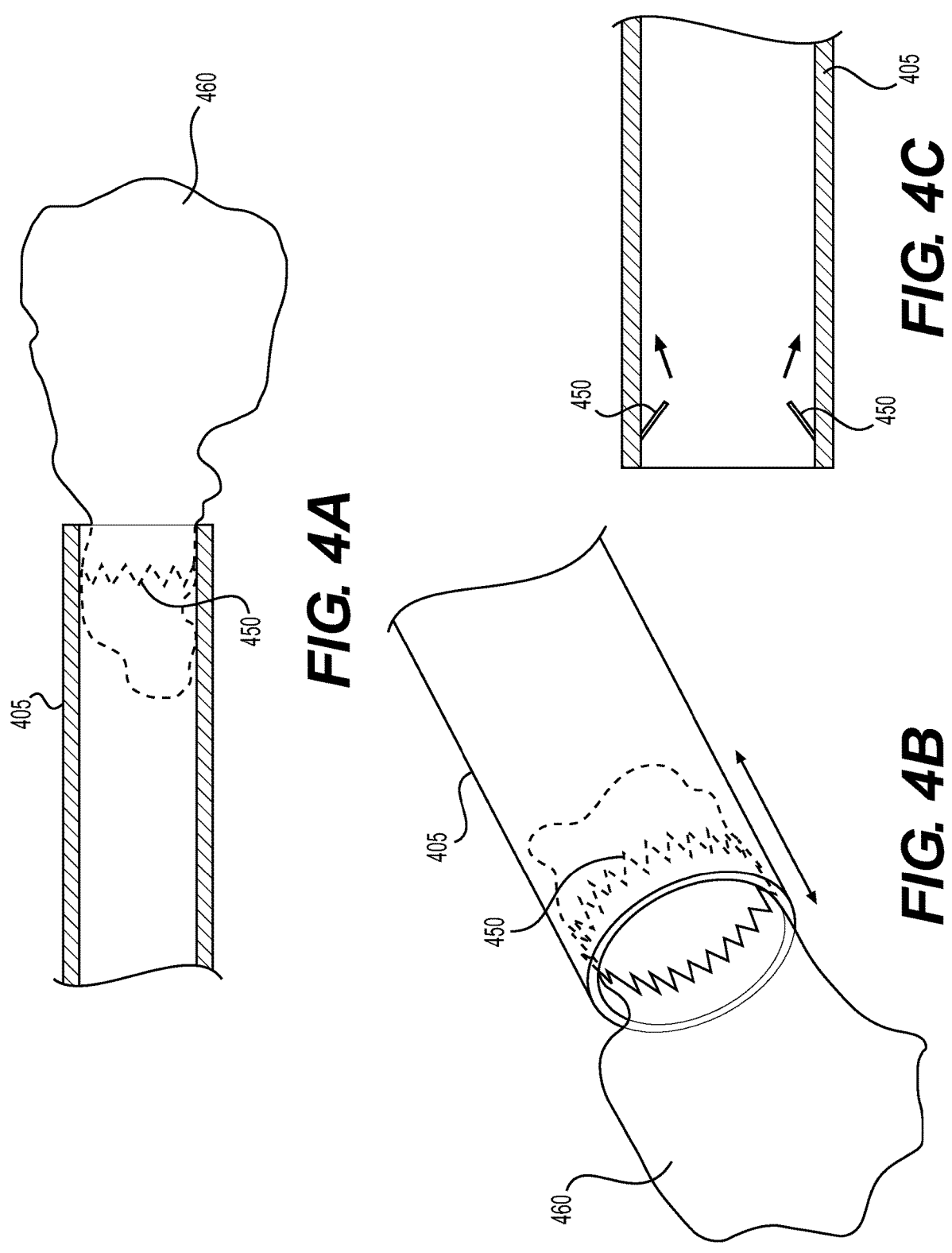
FIG. 4A is an axial cross-sectional view of a distal section of yet another example aspiration catheter including a inner ring of deflectable proximal facing saw teeth acting as the non-powered internal structural impediment in accordance with the present disclosure.
FIG. 4B is a perspective view of the distal section of the aspiration catheter of FIG. 4A.
FIG. 4C is an axial cross-sectional view depicting the deflection of two of the saw teeth in the proximal direction.

In still another example shown in the axial cross-sectional views in FIGS. 4A-4C, the aspiration catheter 405 includes a ring of saw teeth 450 as the non-powered internal structural impediment. Preferably, the saw teeth 450 are proximal facing (i.e., angled or slanted in a proximal direction) and made of a biocompatible elastomeric polymer material deflectable to accommodate the clot 460 thereover during vacuum pressure. The perspective view of the distal section of FIG. 4B and the axial cross-sectional view of the distal section in FIG. 4C of the aspiration catheter 405 illustrate the saw teeth 450 deflected allowing the clot 460 to pass over while being ingested into the lumen of the aspiration catheter 405 during vacuum pressure. Application of cyclic aspiration results in relative movement back-and-forth (as denoted by the bi-directional arrows in FIG. 4B) between the clot and the ring of saw teeth 450 macerating, severing, cutting up, and tearing up the clot 460. FIG. 4C is a longitudinal cross-sectional view of the distal section of the aspiration catheter 405 showing the saw teeth 450 proximal facing (i.e., angled or slanted in a proximal direction) and deflectable (as denoted by the respective curved arrows) accommodating the clot while passing over during vacuum pressure. Whereas, during an interval of positive pressure, the proximally facing saw teeth 450 impale the clot 460 assisting in fragmenting the clot, restraining the clot minimizing distal movement, and/or altering the shape of the clot (e.g., elongate).

Figures 5A, 5B:
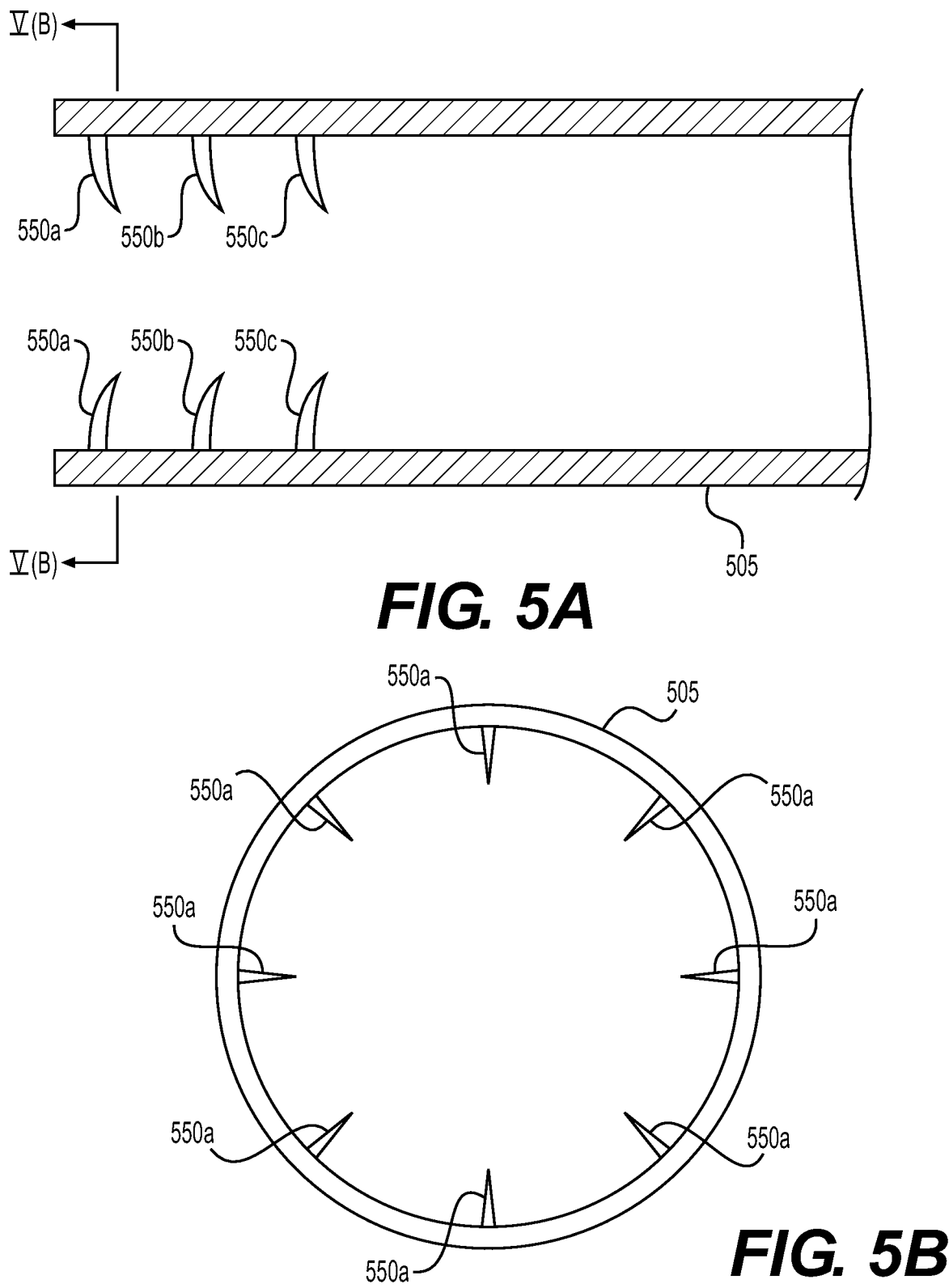
FIG. 5A is an axial cross-sectional view of a distal section of still another example aspiration catheter including a plurality of rings of teeth arranged in series one after the other in the axial direction acting as the non-powered internal structural impediment in accordance with the present disclosure.
FIG. 5B is a distal end view of the aspiration catheter of FIG. 5A.

Rather than a continuous ring of saw teeth as in FIG. 4A-4C, a plurality of individual spikes or teeth 550 separated from one another (resembling tines on a fork or teeth of a piranha) may be arranged along the inner wall of the aspiration catheter 505. The individual spikes or teeth 550 are secured at one end to the inner wall of the aspiration catheter 505, while its opposite free end is preferably proximal facing (i.e., angled or slanted in a proximal direction)(FIG. 5A). During an interval of positive pressure, the proximally facing spikes or teeth 550 impale the clot assisting in fragmenting the clot, restraining the clot minimizing distal movement, and/or altering the shape of the clot (e.g., elongate). A plurality of rings of spikes or teeth 550a, 550b, 550c (i.e., the spikes or teeth in any one ring being in the same radial plane) may be arranged in series in an axial direction wherein the size (i.e., extent to which the spikes or teeth project radially inward into the lumen of the aspiration catheter 505) of the spikes or teeth of any particular ring 550a, 550b, 550c reduces in a proximal direction relative to those more distally thereto (FIG. 5A). That is, the spikes or teeth in the ring 550a are larger than the spikes or teeth in the ring 550b which, in turn, are greater than the spikes or teeth in the ring 550c. Preferably, the spikes or teeth in any one ring 550a, 550b, 550c (i.e., within the same radial plane) are substantially equal in size.

Figures 7A, 7B:
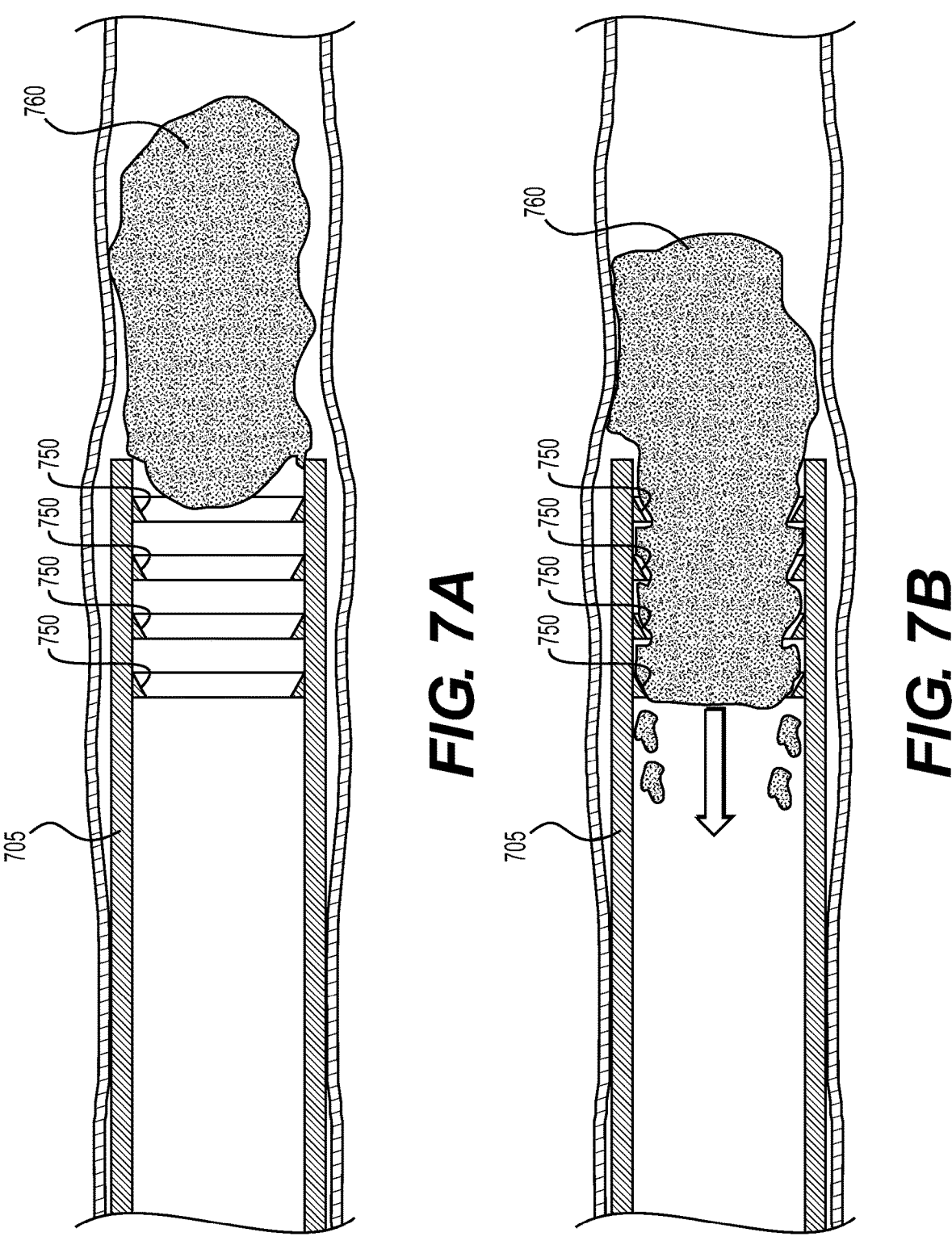
FIG. 7A is an axial cross-sectional view of a distal section of still another example aspiration catheter with a section of the inner wall having a tapered rib inner contour acting as the non-powered internal structural impediment in accordance with the present disclosure.
FIG. 7B is an axial cross-sectional view of the aspiration catheter of FIG. 7A depicting the clot engaging with the tapered rib inner contour tearing apart pieces of the outer contour thereof during the vacuum pressure interval of cyclic aspiration.

An inner wall of the aspiration catheter 705, otherwise an inner lining permanently secured thereto, may have a distal section thereof forming a molded non-uniform inner diameter serving as the non-powered internal structural impediment. FIGS. 7A & 7B depict a section of the inner wall of the aspiration catheter 705 having a plurality of circumferential tapered molded or thermoformed ribs 750 arranged in series, one after the other, in the axial direction. Each of the plurality of circumferential molded or thermoformed ribs 750 preferably being tapered with its widest diameter closest to the distal tip/end of the aspiration catheter 705 and its narrowest diameter farther from the distal tip/end of the aspiration catheter 705. Furthermore, the molded or thermoformed edges of the circumferential profile may optionally be sharp fostering the maceration, severing, or tearing up of the outer surface of the clot 760 during engagement therewith. During vacuum pressure, the clot 760 engages with the molded ribs 750 assisting in ingestion; whereas during positive pressure, the molded ribs 750 minimize distal spring-back (e.g., relaxation) of the clot 760 in a distal direction and/or cause the clot to change shape (e.g., elongate).

Figures 8A, 8B, 8C:
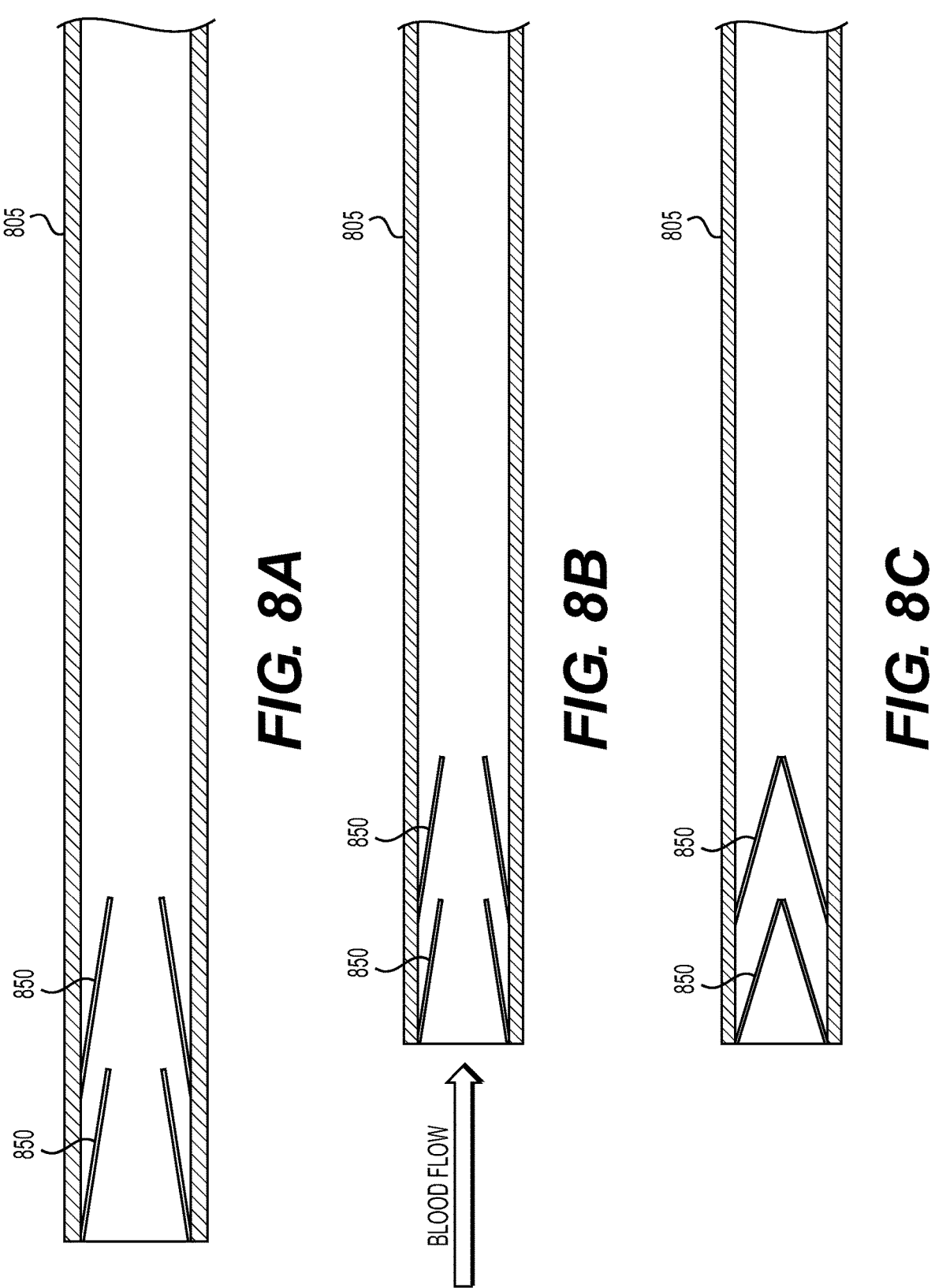
FIG. 8A is an axial cross-sectional view of a distal section of yet another example aspiration catheter including two sets of flaps arranged in series one after the other in an axial direction acting as the non-powered internal structural impediment in accordance with the present disclosure.
FIG. 8B is an axial cross-sectional view of the aspiration catheter of FIG. 8A while undergoing blood flow or vacuum pressure during cyclic aspiration with the flaps in an open state allowing passage therethrough of the blood.
FIG. 8C is an axial cross-sectional view of the aspiration catheter of FIG. 8A while subject to the positive pressure interval during cyclic aspiration with the flaps in a closed state prohibiting back flow of the blood therethrough in a distal direction.
Figures 8D, 8E, 8F:
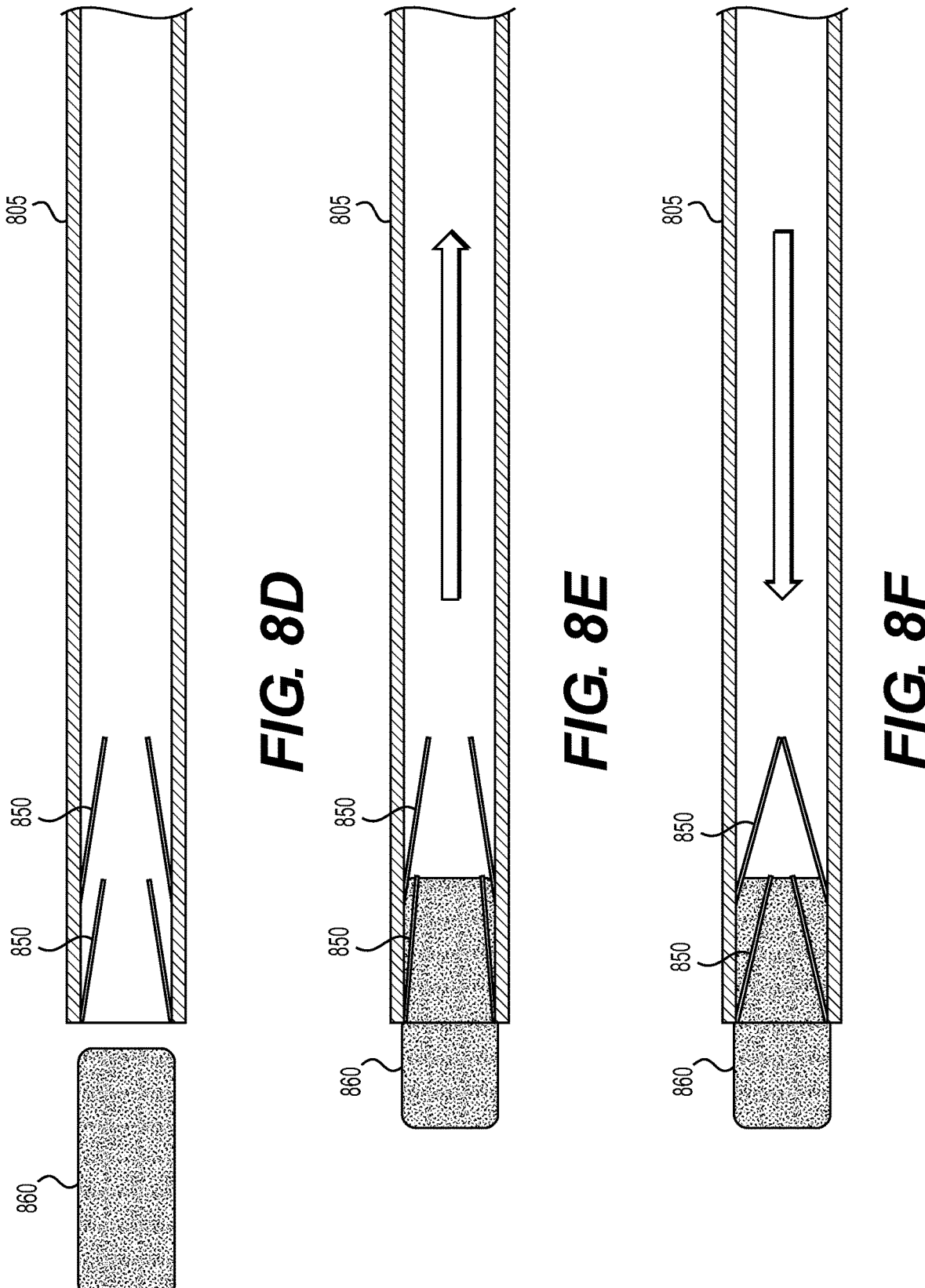
FIG. 8D is an axial cross-sectional view of the distal section of the aspiration catheter of FIG. 8A depicted advanced to a proximal side of the targeted clot prior to applying cyclic aspiration; wherein the flaps are depicted in an open state.
FIG. 8E is an axial cross-sectional view of the distal section of the aspiration catheter of FIG. 8A depicted subject to the vacuum pressure interval during cyclic aspiration depicting the widening of the flaps to accommodate the clot as it is ingested into the aspiration catheter.
FIG. 8F is an axial cross-sectional view of the distal section of the aspiration catheter of FIG. 8A depicted subject to the positive pressure interval during cyclic aspiration transitioning the flaps to a closed state clamping/pinching/restraining therein the ingested clot preventing expulsion from the aspiration catheter while simultaneously aiding in tearing apart the clot apart.
Figure 10A:
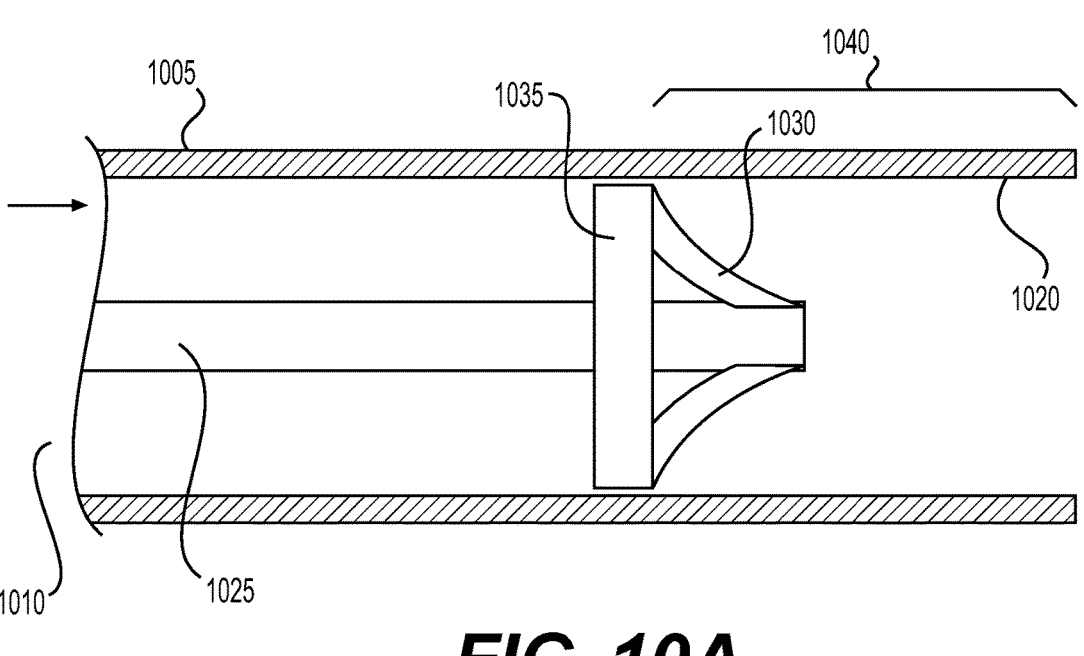
FIG. 10A is a cutaway axial view of a distal section of an example separate non-powered internal structural impediment in accordance with the present disclosure slidable in the lumen of an aspiration catheter.
Figure 10B:
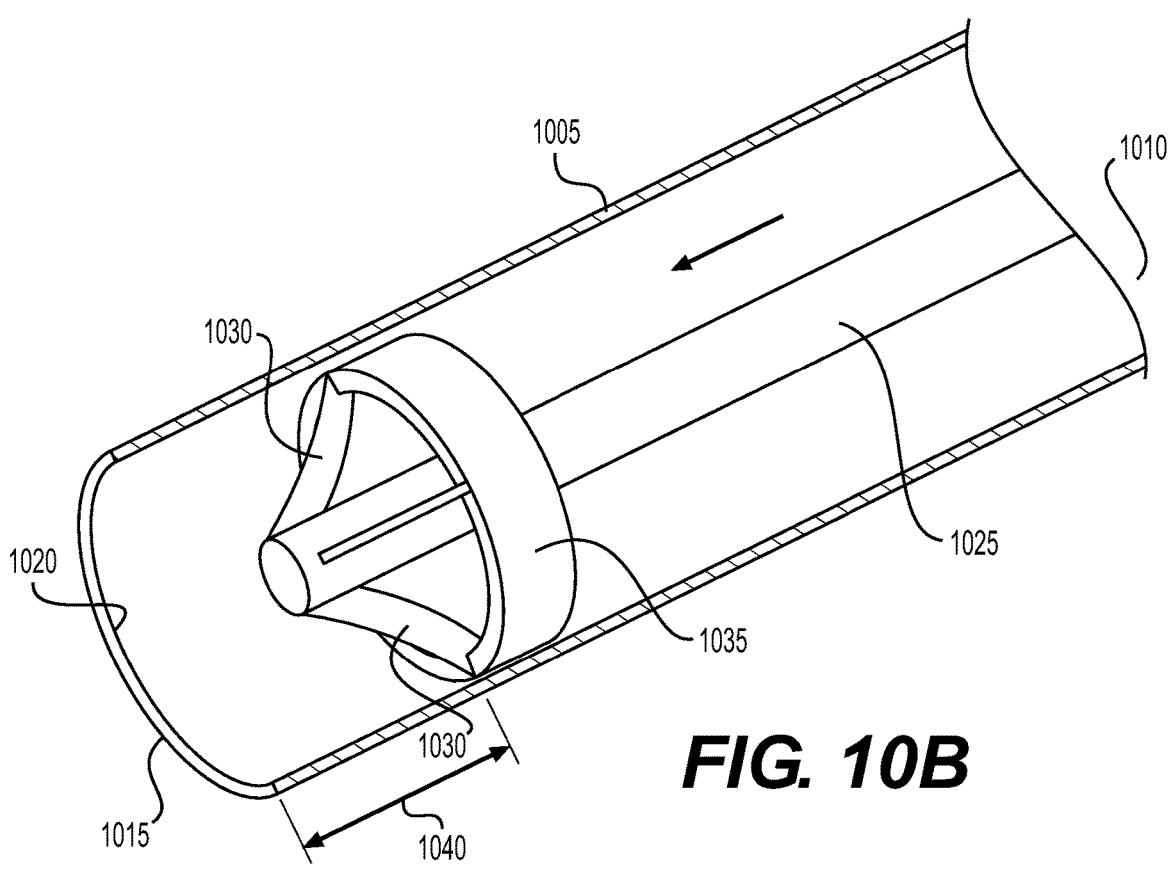
FIG. 10B is a cutaway perspective downward view of the aspiration catheter with the separate internal structural impediment in the lumen thereof of FIG. 10A.
Figures 10C, 10D:
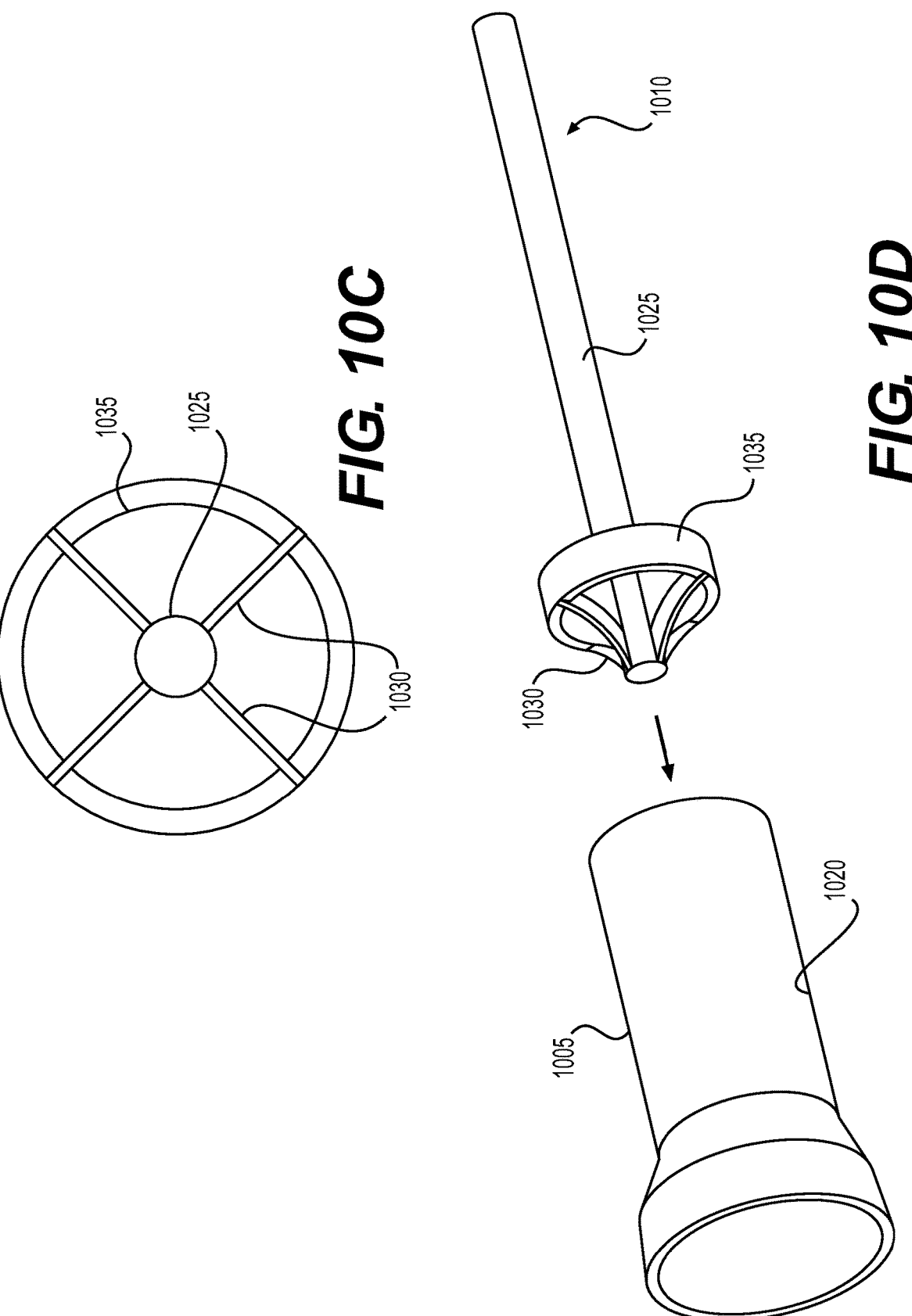
FIG. 10C is a distal end view of the internal structural impediment of FIG. 10A.
FIG. 10D is an exploded view of the aspiration catheter and non-powered internal structural impediment of FIG. 10A.

In a still yet further example, the internal structural impediment may be flaps 850 arranged in the distal section of the lumen of the aspiration catheter 805. The flaps 850 are preferably made of a polymer material and transitionable between an open state and a closed state in response to cyclic aspiration. FIG. 8A depicts an example aspiration catheter 805 with two sets of flaps 850 arranged in series, one after the other, in an axial/longitudinal direction. Any number of sets of flaps are contemplated, preferably more than one, most preferably two. Each flap is secured at a distal end to the inner wall of the aspiration catheter 805. An opposite free proximal end of the flap is displaceable between an open state (separated a maximum distance from one another) and a closed state (drawn together preferably physically contacting one another). During positive pressure, the flaps 850 are maintained in an open state allowing the passage of blood flow therethrough (FIG. 8B, prior to ingestion of the clot). Subject to the positive pressure, the flaps 850 transition to a closed state prohibiting flow of the blood therethrough in a distal direction (FIG. 8C, prior to ingestion of the clot). Opening and closing of the flaps 850 while ingesting the clot therein is illustrated in FIGS. 8D-8F. Prior to applying the cyclic aspiration pressure waveform, in a preliminary step of the thrombectomy procedure the distal end of the aspiration catheter 805 is advanced through the vessel to a proximal side/face of the clot 860 (FIG. 8D). During this preliminary step the flaps 850 are in an open state. With the aspiration catheter properly positioned within the vessel, the cyclic aspiration pressure waveform is then applied. As depicted in FIG. 8E, during application of vacuum pressure (as denoted by the right-hand arrow), the clot 860 is ingested in a proximal direction into the distal end of the aspiration catheter 805 while the flaps 850 are in the open state. While being ingested, if the clot is sufficiently large in diameter, the flaps 850 (already in an open state) may be further displaced even wider (i.e., greater separation of the respective free proximal ends from one another) to accommodate the clot passing therethrough. This enhanced, greater, or heightened widening of an already open state of the flaps 850 disposed closest to the distal end of the catheter accommodating the clot while passing therethrough is depicted in FIG. 8E in comparison to the smaller separation of the flaps 850 proximal thereto the clot has yet to traverse. Subsequent application thereafter of the positive pressure, depicted in FIG. 8F, closes the flaps 850. Employing multiple sets of flaps in an axial direction provides a synergistic benefit resulting from the individual performance of each set of flaps 850 while in a closed state, as shown in FIG. 8F. That is, the closing of those most distal set of flaps 850 clamps or pinches the clot ingested therein simultaneously minimizing risk of escape during positive pressure while also aiding in tearing it apart. In concert therewith, the closing of the set of flaps 850 proximally thereto (yet to be traversed by the clot) prohibits the back flow of blood therethrough when subject to positive pressure. For this reason, the non-powered internal structural impediment preferably includes at least two sets of flaps 850 arranged in series, one after the other, in the axial direction. Accordingly, movement of the flaps in FIG. 8A-8F may be in response to: (i) the cyclic aspiration pressure waveform (i.e., vacuum pressure & positive pressure); (ii) movement of the clot through the aspiration catheter during vacuum pressure widening the opening between the flaps to accommodate passage therethrough; and/or (iii) movement of an auxiliary device when advanced in a distal direction through the aspiration catheter widening the opening of the flaps to accommodate passage therethrough.

Figures 6A, 6B:
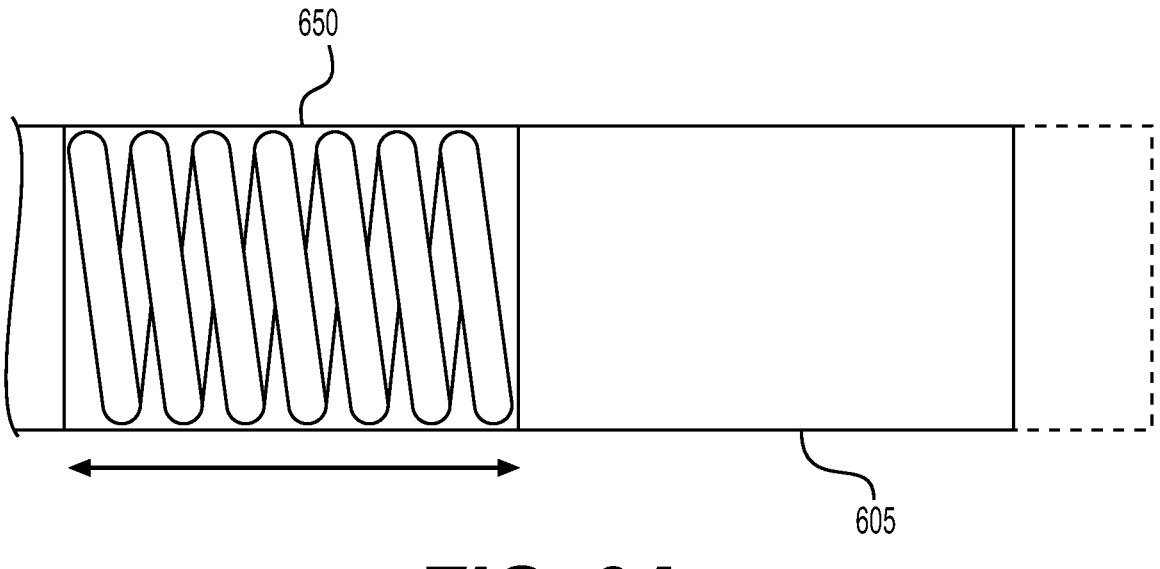
FIG. 6A is a side view of a distal section of yet another example aspiration catheter including an axially compressible spring section acting as a supplemental non-powered internal structural impediment generating a supplemental vibrating effect which when combined with any other example disclosed herein of the non-powered internal structural impediment arranged distally thereof producing a primary vibrating effect while paired with cyclic aspiration assists in tearing apart the clot, wherein the axially compressible spring section is depicted in an axially expanded state.
FIG. 6B is a side view of the distal section of the aspiration catheter of FIG. 6B wherein the axially compressible spring section is depicted in an axially compressed state.

With any of the previously described examples when subject to cyclic aspiration the clot is subjected to a primary vibration effect during relative movement (i.e., back-and forth) in an axial direction between the clot and the non-powered internal structural impediment. The efficiency by which the clot is torn apart may be fostered or optimized by imparting a supplemental vibration effect in addition to that of the primary vibration effect. In the example of FIGS. 6A & 6B, the secondary vibration effect is compression or squeezing in an axial direction between the clot and the non-powered internal structural impediment. This supplemental vibration effect of axial compression may be achieved by the aspiration catheter 605 including an axially compressible spring section 650, depicted in both an expanded state (i.e., non-compressed or non-constricted) (FIG. 6A) and compressed state (i.e., collapsed or constricted) (FIG. 6B). The axially compressible spring section 650 may be made, for example, using a spiral coil or a section of material of reduced durometer (e.g., similar to a Chinese lantern). When subject to cyclic aspiration, the clot simultaneously undergoes a primary vibration effect, i.e., back-and-forth movement in the axial direction (as denoted by the bidirectional arrow left and right) of relative movement between the clot and any one of the heretofore described example non-powered internal structural impediments. Simultaneously therewith the axially compressible spring section 650 when subject to cyclic aspiration imparts a supplemental vibration effect alternatingly contracting (FIG. 6B) and expanding (FIG. 6A)(as denoted by the respective bi-directional arrows) thereby compressing and elongating the clot therein analogous to that of a jack-hammer. Accordingly, the severing, dividing, or tearing apart of the clot is more efficient when during cyclic aspiration the primary vibration effect (i.e., back-and-forth movement) imposed on the clot utilizing any one of the aforementioned example non-powered internal structural impediments and the supplemental vibration effect of axially compressing and elongating of the clot occur simultaneously.

The preceding examples describe the non-powered internal structural impediment permanently secured in an axial position within the lumen of the aspiration catheter. Whereas the examples described hereafter are all directed to the non-powered internal structural impediment as a separate device or component independent and slidable within the lumen of the aspiration catheter.

In the example in FIGS. 10A-10D, the cyclic aspiration catheter system includes an aspiration catheter 1005 having a lumen 1020 defined therein. The system further includes a non-powered internal structural impediment 1010 as a separate component slidably receivable (i.e., pushable in the distal direction) within the lumen 1020 of the aspiration catheter 1005, as shown in the exploded view in FIG. 10D. In the example in FIGS. 10A-10D, the non-powered internal structural impediment includes a shaft 1025 (i.e., pushing member) extending in an axial direction with a severing head secured to a distal end of the shaft 1025. The severing head optionally includes an outer circular frame 1035 arranged concentrically with the shaft 1025. As illustrated in the side view of FIG. 10A, preferably the outer circular frame 1035 is arranged proximally relative to the distal end of the shaft 1025. A plurality of blades 1030 are secured between the distal end of the shaft 1025 and the outer circular frame 1035. Alternatively, the outer circular frame 1035 may be eliminated altogether with each blade 1030 secured only at one end to the shaft 1025 while the opposite end is free (i.e., not attached to any other component). Each of the blades 1030 preferably has a sharp distal facing edge to foster the severing, dividing, cutting up, or tearing apart of the clot moving relative thereto when subject to cyclic aspiration. To further assist in severing the clot, the blades rather than projecting radially outward perpendicularly relative to the shaft 1025 are preferably angled in a proximal facing direction at an acute angle relative to the shaft 1025. That is, preferably the blades are arranged so that their respective proximal ends are arranged within a first common radial plane while the respective distal ends are arranged within a second common radial plane distally relative to that of the first common radial plane. In a proximal direction, the blades 1030 depicted in FIG. 10A-10D slant proximally outwards away from the shaft 1025, but may alternatively be arranged in the opposite direction slanting proximally inwards towards the shaft 1025. In addition, the distal facing edge of each blade 1050 in the example in FIGS. 10A-10D has a concave contour or profile to assist in severing the clot, but it is also possible to have a convex or straight profile. FIGS. 10A-10D illustrate an example of the severing head with four blades 1030 equidistantly spaced radially. However, any number of one or more blades and their arrangement on the severing head may be selected, as desired. Once the non-powered internal structural impediment 1010 is properly positioned within the aspiration catheter it may optionally be locked in place (e.g., tightening a proximal hemostasis valve attached to catheter hub around its shaft) or simply held in position by the interventionalist.

In operation, either in series one after the other or together as an assembled unit the aspiration catheter 1005 and separate non-powered internal structural impediment 1010 are delivered through the vessel to the target site on the proximal side of the target clot to be captured. When the two separate components are navigated through the vessel in series one after the other, the aspiration catheter 1005 is delivered first through the vessel to the target site on the proximal side/face of the target clot. Once the aspiration catheter 1005 is properly positioned within the vessel at the target site, using the shaft 1025 the non-powered internal structural impediment 1010 thereafter is advanced (i.e., pushed or slid) in a distal direction through the lumen 1020 of the aspiration catheter 1005. Advancement of the non-powered internal structural impediment 1010 into the lumen 1020 of the aspiration catheter 1005 ceases proximally of the distal tip/end preferably leaving a free space 140 between the respective distal ends of the aspiration catheter 1005 and the non-powered internal structural impediment 1010. Alternatively, when the two separate components are navigated through the vessel together as an assembled unit, prior to introduction into the body, using the shaft 1025 the non-powered internal structural impediment 1010 is advanced (i.e., slid or pushed) through the lumen 1020 to the desired position proximally of the distal tip of the aspiration catheter 1005 forming the assembled unit. The assembled unit is then delivered through the vessel to the target site on the proximal side/face of the target clot. Regardless of whether the aspiration catheter 1005 and non-powered internal structural impediment 1010 are delivered through the vessel to the target site either in series or together as the assembled unit, once properly positioned at the target site cyclic aspiration is applied to capture the clot. The non-powered internal structural impediment 1010 does not require its own power source or associated components (e.g., motor, gears, etc.) to impart axial vibration and/or rotation thereto. Rather, the clot is severed exclusively by leveraging the kinetic energy imparted by the cyclic aspiration pressure waveform inducing movement of the clot relative to non-powered internal structural impediment as well as inducing axial vibration to the non-powered internal structural impediment including the cutting elements associated therewith. Simplifying and minimizing the number of components of the non-powered internal structural impediment in this manner, minimizes the bulkiness, footprint, weight, and expense of the cyclic aspiration system in accordance with the present disclosure.

Another example of the non-powered internal structural impediment in accordance with the present disclosure is shown in FIGS. 11A-11D. The non-powered internal structural impediment (shown in the side view in FIG. 11A) is a wire 1125 (e.g., a guide wire) having a plurality of cutting elements (e.g., teeth or jagged edge(s)) 1130 disposed along a distal section thereof. Cutting elements 1130 may be made of a biocompatible polymer material and the number of which may be selected, as desired. Moreover, the shape and size of each of the cutting elements 1130 may be same or different. The cutting elements 1130 are preferably angled or slanted in a proximal direction deflectable to allow passage of the clot thereover while being ingested into the distal tip/end of the aspiration catheter during vacuum pressure. During positive pressure, the proximal slanted cutting elements 1130 impale the clot tearing it apart, restraining the clot in place minimizing distal movement and/or altering its shape (e.g., elongate). If the clot is lodged in place when impaled by the cutting elements 1130, a maximized level of positive pressure may be imposed without risk of expulsion of the clot from the distal end/tip of the aspiration catheter.

Figures 11A, 11B:
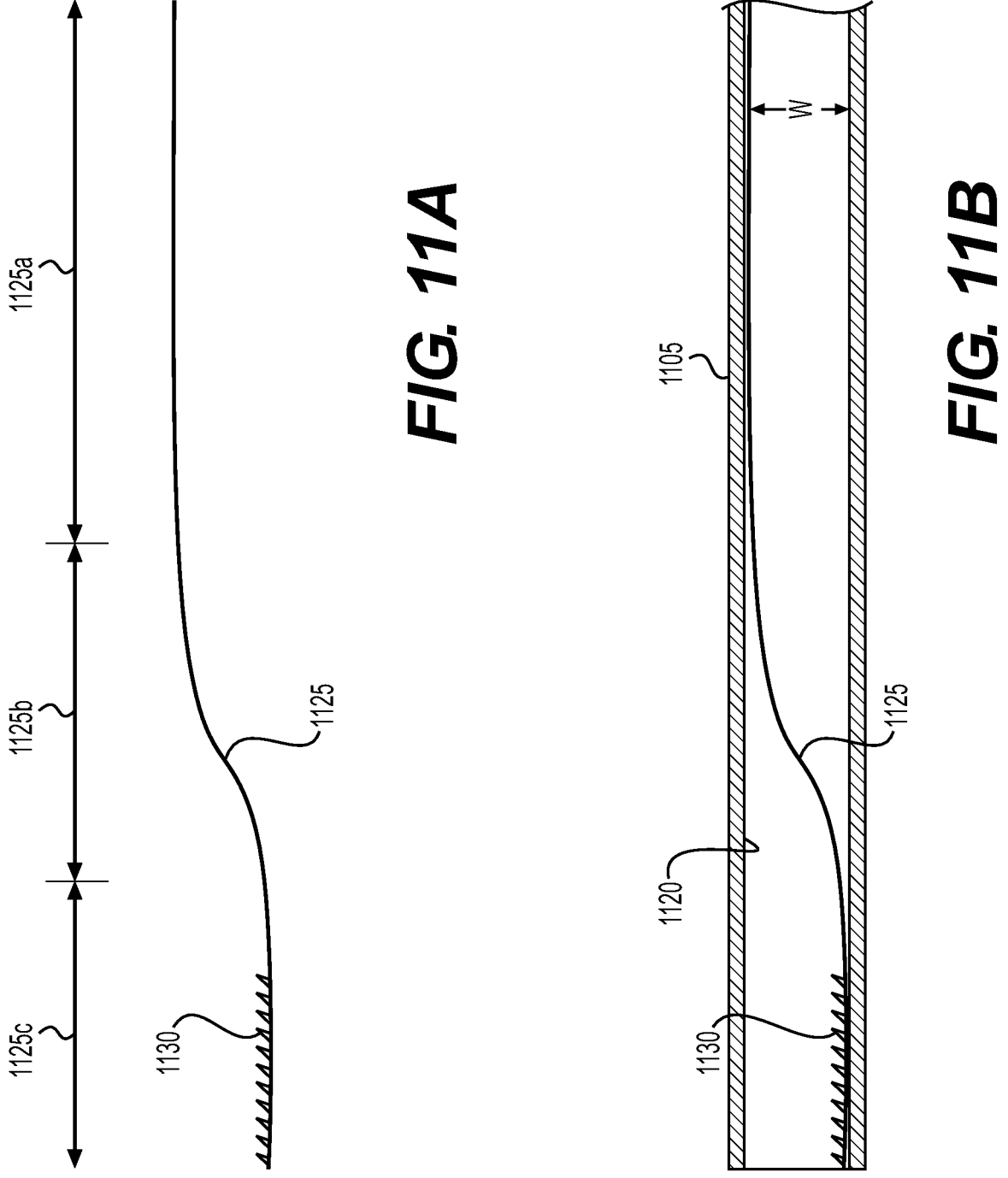
FIG. 11A is a side view of another example of a separate non-powered internal structural impediment as a single preformed wire in accordance with the present disclosure slidable through a lumen of an aspiration catheter.
FIG. 11B is a cutaway axial view of an aspiration catheter with the single preformed wire in FIG. 11A advanced through the lumen thereof.
Figures 11C, 11D:
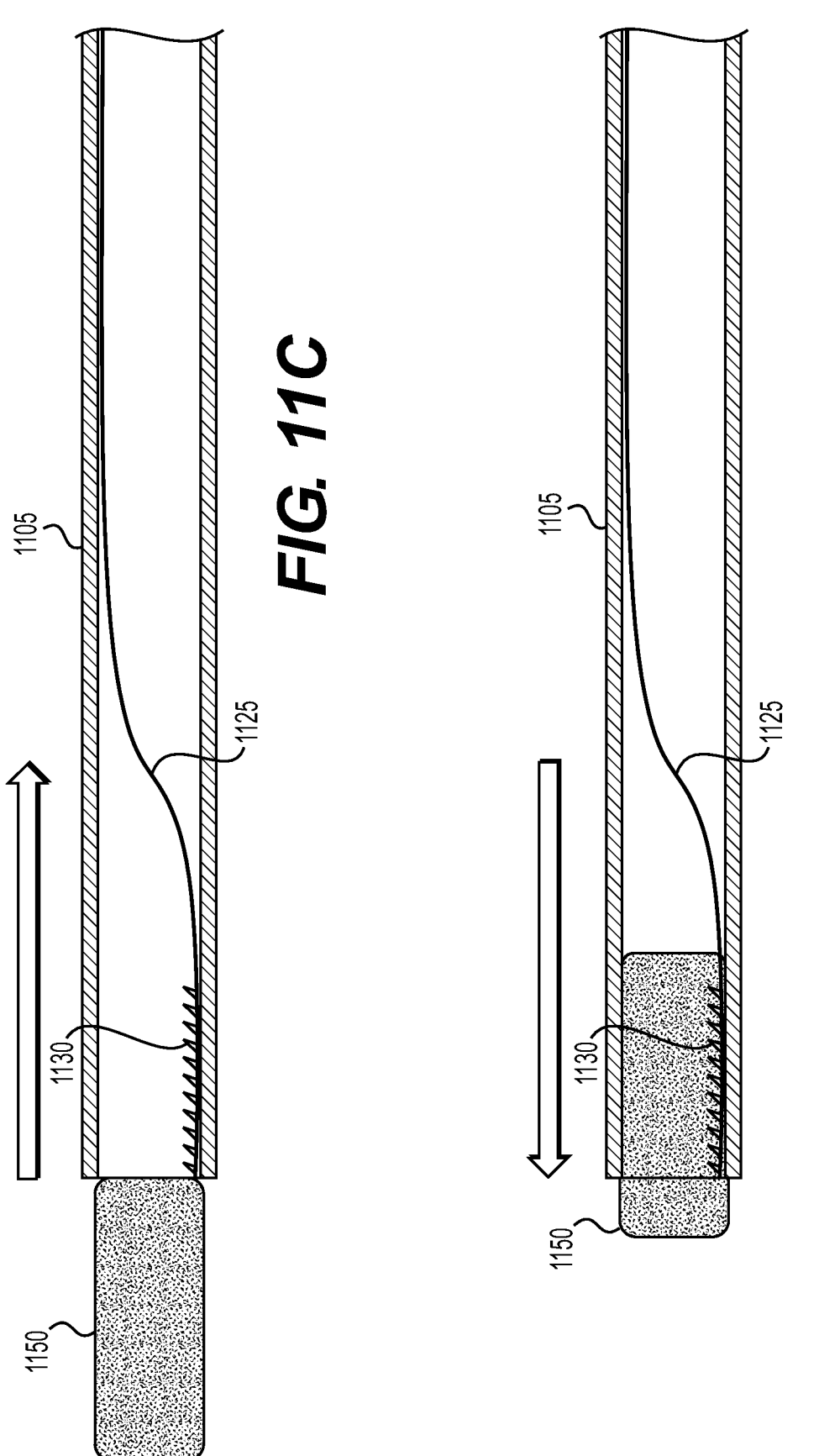
FIG. 11C is a cutaway axial view of the aspiration catheter with the single preformed wire in FIG. 11A advanced through the lumen thereof, depicted during the vacuum pressure interval of cyclic aspiration drawing a clot to the distal tip/end of the aspiration catheter.
FIG. 11D is a cutaway axial view of the aspiration catheter with the single preformed wire in FIG. 11A advanced through the lumen thereof, depicted during the positive pressure interval of cyclic aspiration illustrating the clot impaled by the teeth of the single preformed wire.
Figure 11E:
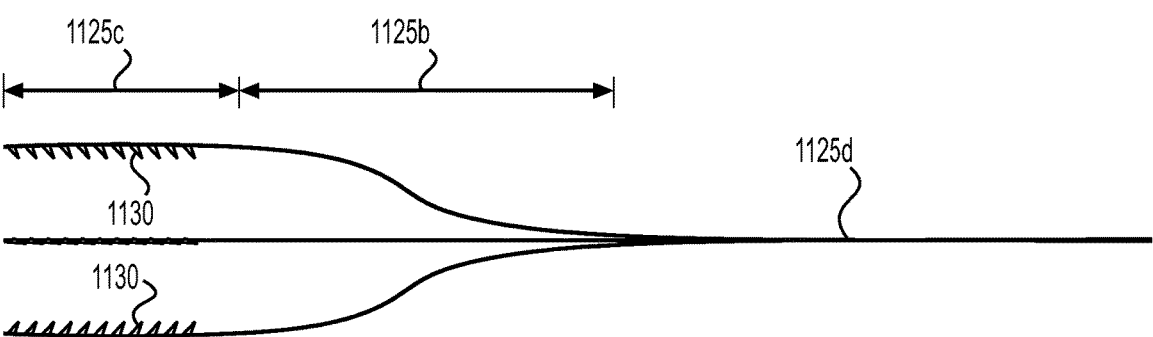
FIG. 11E is a side view of another example of a separate non-powered internal structural impediment of four preformed wires in accordance with the present disclosure.
Figure 11F:
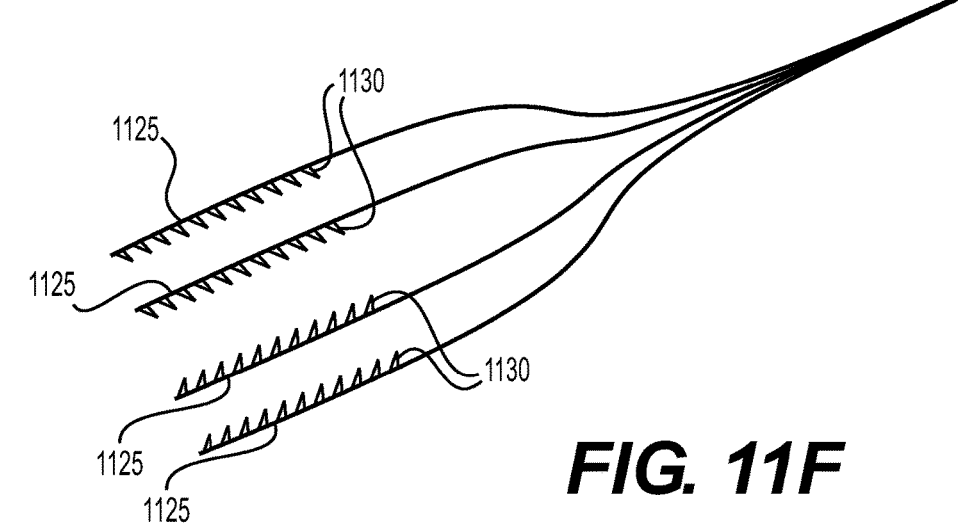
FIG. 11F is a perspective downward view of the four preformed wires of FIG. 11E.
Figure 11G:
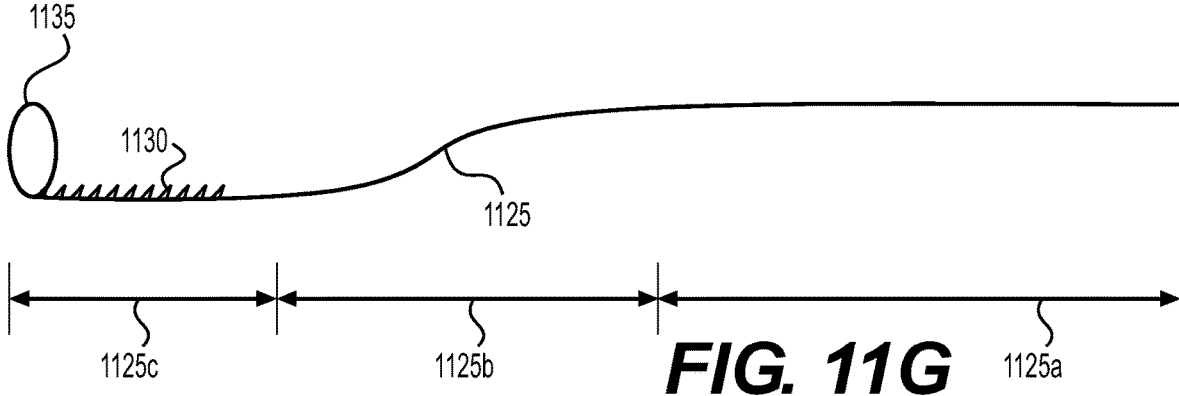
FIG. 11G is a side view of still another example of a separate non-powered internal structural impediment as a single wire with a reinforcement loop disposed at the distal end thereof to maintain proper positioning of the teeth.

Wire 1125 is molded or heat set to a preformed desired shape. In a preferred configuration shown in FIG. 2A, wire 1125 is preformed to have a linear (i.e., straight) proximal section 1125a, a linear (i.e., straight) distal section 1125c substantially parallel thereto, and a non-linear transition section 1125b therebetween. Preferably the preformed shape of the wire 1125 is such that when divided midway in an axial direction the distal half is flipped both axially and laterally relative to the proximal half. Linear proximal section and distal sections 1125a, 1125c extend in an axial direction separated a predetermined distance (i.e., width W) from one another in a lateral direction by the transition section 1125c. While forming the wire 1125, the predetermined distance separation (i.e., width W) of the linear proximal and distal sections 1125a, 1125c relative to one another in the lateral direction is preferably substantially equal to the inner diameter of the lumen 1120 of the aspiration catheter 1105 into which the non-powered internal structural impediment 1125 is to be advanced. Accordingly, as shown in FIG. 11B, when the non-powered internal structural impediment 1125 is introduced, slid, or advanced into the lumen 1140 of the aspiration catheter 1105, the respective linear proximal and distal sections 1125a, 1125c physically directly contact the inner wall of the lumen 1140 of the aspiration catheter 1105 ensuring a maximum open space within the lumen 1140 radially inward of the cutting elements (e.g., teeth 1130) into which the clot may be ingested. To maintain the linear distal section 1125c of the wire 1125 substantially in direct physical contact with the inner wall of the lumen of the aspiration catheter and thereby ensure that the cutting elements 1130 (e.g., teeth) are properly positioned projecting into the lumen, a distal tip/end of the wire 1135 itself or a separate wire segment attached thereto may be formed into a distal loop or ring 1135 (FIG. 11G). Distal loop or ring 1135 is closed but may be open forming a "C" shape.

More than one wire may be used to form the non-powered internal structural impediment. FIGS. 11E & 11F are side and perspective views, respectively, of an example multi wire non-powered internal structural impediment formed using four wires 1125. Staring at the distal tip/end, each of the four wires 1125 includes a linear distal section 1125c, a transition section 1125b, and a linear proximal section 1125d. The linear proximal section 1125b where each the four wires meet may be twisted together to provide additional reinforcement and support as the pushing member when advancing the non-powered internal structural impediment in a distal direction through the lumen to the desired position in the distal section of the aspiration catheter. Alternatively, each of the four wires 1125 may be joined at their respective proximal ends to a separate fifth wire extending in a proximal direction and serving as the pushing member when advancing the non-powered internal structural impediment in a distal direction through the lumen to the desired position in the distal section of the aspiration catheter. The four wires 1125 are radially spaced equidistantly from each other in FIGS. 11E & 11F, but may be arranged as desired. Furthermore, the arrangement of the preformed wires 1125 is such that their linear distal sections 1125c are substantially in direct physical contact with the inner wall of the lumen of the aspiration catheter when advanced therein. A plurality of cutting elements 1130 (e.g., jagged teeth) are secured along a distal section of some, preferably all, of the wires 1125. By way of illustrative example, the non-powered internal structural impediment in FIGS. 11E & 11F is formed with four wires, but any number of two or more wires may be used. As with the single wire in FIG. 11G, a single distal loop or ring (closed or open forming a "C") may be secured to each of the respective distal ends of the four wires 1125 to maintain proper positioning of the cutting elements 1130 (e.g., teeth).

In operation, either in series one after the other or together as an assembled unit the aspiration catheter 1105 and separate non-powered internal structural impediment 1125 (e.g., single wire or multiple wires joined together) are delivered through the vessel to the target site on the proximal side/face of the target clot to be captured. When the two separate components are navigated through the vessel in series independently of one another, the aspiration catheter 1105 is delivered first through the vessel to the target site on the proximal side/face of the target clot. Once the aspiration catheter 1105 is properly positioned within the vessel at the target site, using the proximal end the non-powered internal structural impediment 1125 (e.g., single wire or multiple wires joined together) thereafter is advanced (i.e., pushed or slid) in a distal direction through the lumen 1120 of the aspiration catheter 1105. Advancement of the non-powered internal structural impediment 1125 (e.g., single wire or multi wires joined together) into the lumen 1120 of the aspiration catheter 1105 ceases proximally of the distal tip/end of the aspiration catheter 1105. Alternatively, when the two separate components are navigated through the vessel together as an assembled unit, prior to introduction into the body, using the proximal end the non-powered internal structural impediment 1125 (e.g., single wire or multi wires joined together) is advanced (i.e., slid or pushed) through the lumen 1120 to the desired position in the distal section of the aspiration catheter 1105 proximally of the distal tip/end forming the assembled unit. The assembled unit is then delivered through the vessel to the target site on the proximal side/face of the target clot. Regardless of whether the aspiration catheter 1105 and non-powered internal structural impediment 1125 (e.g., single wire or multi wires joined together) are delivered through the vessel to the target site either in series or together as the assembled unit, once properly positioned at the target site cyclic aspiration is applied to capture the clot. Neither the non-powered internal structural impediment 1125 (e.g., single wire or multi wires joined together) nor the cutting elements 1130 associated therewith require its own power source or associated components (e.g., motor, gears, etc.) to impart axial vibration and/or rotation. Rather, the clot is severed exclusively by leveraging the kinetic energy imparted by the cyclic aspiration pressure waveform inducing relative movement between the clot and the cutting elements 1130 disposed along a distal section of the non-powered internal structural impediment 1125 (e.g., single wire or multi wires joined together). Simplifying and minimizing the number of components of the non-powered internal structural impediment in this manner, minimizes the bulkiness, footprint, weight, and expense of the cyclic aspiration system in accordance with the present disclosure.

For each of the non-powered internal structural impediment examples (e.g., FIGS. 10A-10D & 11A-11G) described above representing a separate component independent of and slidable within the lumen of the aspiration catheter a tight seal is provided between the catheter hub and the shaft or wire by which the non-powered internal structural impediment is advanced to ensure the cyclic aspiration pressure waveform is not impacted.

Aspects of the present disclosure are also provided by the following numbered clauses:

Clause 1

A cyclic aspiration system comprising: an aspiration catheter (105) having a proximal end (110), an opposite distal end (115), respective outer and inner walls extending in a longitudinal direction from the proximal end (110) to the distal end (115) defining therein a lumen; a cyclic aspiration source (1200) connected in fluid communication to the proximal end (110) of the aspiration catheter (105); the cyclic aspiration pressure source (1200) producing a cyclic aspiration pressure waveform of intermittently cycling intervals of a vacuum pressure below atmospheric pressure and a positive pressure higher than the vacuum pressure; and a non-powered internal structural impediment (150, 150', 250, 350, 350', 450, 550, 650, 750, 850, 950, 1010, 1125) disposed within the lumen of the aspiration catheter and configured to engage with a clot capturable therein during resulting movement between the clot and the non-powered internal structural impediment (150, 150', 250, 350, 350', 450, 550, 650, 750, 850, 950, 1010, 1125) while subject to the cyclic aspiration pressure waveform.

Clause 2

The cyclic aspiration system of Clause 1, wherein the engagement of the clot capturable therein with the non-powered internal structural impediment (150, 150', 250, 350, 350', 450, 550, 650, 750, 850, 950, 1010, 1125) resulting in: (i) disrupting a structure of the clot capturable therein from that of a single unitary mass into a plurality of clot pieces; (ii) altering a shape of at least a portion of the clot capturable therein; and/or (iii) restricting distal movement of the clot capturable therein.

Clause 3

The cyclic aspiration system of any of Clauses 1 through 2, wherein movement between the clot and the non-powered internal structural impediment (150, 150', 250, 350, 350', 450, 550, 650, 750, 850, 950, 1010, 1125) is bi-directional.

Clause 4

The cyclic aspiration system of any of Clauses 1 through 3, wherein the non-powered internal structural impediment (150, 150', 250, 350, 350', 450, 550, 650, 750, 850, 950, 1010, 1125) projects into or spans at least a portion of the lumen of the aspiration catheter (105).

Clause 5

The cyclic aspiration system of any of Clauses 1 through 4, wherein the non-powered internal structural impediment (150, 150', 250, 350, 350',450, 550) is a wire, a fiber, a strut, a rib, teeth, blades, or spikes.

Clause 6

The cyclic aspiration system of any of Clauses 1 through 4, wherein the non-powered internal structural impediment is flaps (850) transitionable between an open state and a closed state.

Clause 7

The cyclic aspiration system of any of Clauses 1 through 4, wherein the non-powered internal structural impediment is a section (750) along the inner wall of the lumen of the aspiration catheter (105) having a non-uniform contour.

Clause 8

The cyclic aspiration system of any of Clauses 1 through 7, further comprising a supplemental non-powered internal structural impediment as a section (650) of the aspiration catheter (105) axially compressible and expandable together with the clot capturable therein in response to the cyclic aspiration pressure waveform.

Clause 9

The cyclic aspiration system of any of Clauses 1 through 8, wherein the non-powered internal structural impediment (150, 150', 250, 350, 350', 450, 550, 650, 750, 850, 950, 1010, 1125) is: (i) permanently secured within the lumen of the aspiration catheter (105); or (ii) a separate component slidable therein the lumen of the aspiration catheter (105) and in the form of a shaft or wire having a plurality of cutting elements.

Clause 10

The cyclic aspiration system of any of Clauses 1 through 9, wherein the cyclic aspiration source (1200) is a pulsatile vacuum pump.

Clause 11

A method for using a cyclic aspiration system including: an aspiration catheter (105) having a proximal end (110), an opposite distal end (115), respective outer and inner walls extending in a longitudinal direction from the proximal end (110) to the distal end (115) defining therein a lumen; a cyclic aspiration source (1200) connected in fluid communication to the proximal end of the aspiration catheter; the cyclic aspiration pressure source producing a cyclic aspiration pressure waveform of intermittently cycling intervals of a vacuum pressure below atmospheric pressure and a positive pressure higher than the vacuum pressure; and a non-powered internal structural impediment (150, 150', 250, 350, 350', 450, 550, 650, 750, 850, 950, 1010, 1125) disposed within the lumen of the aspiration catheter and configured to engage with a clot capturable therein during resulting movement between the clot and the internal structural impediment while subject to the cyclic aspiration pressure waveform; the method comprising the steps of: either simultaneously or in series, advancing through a vessel to a target site on a proximal side of the clot the aspiration catheter (105) and the non-powered internal structural impediment (150, 150', 250, 350, 350', 450, 550, 650, 750, 850, 950, 1010, 1125); applying the cyclic aspiration pressure waveform to the aspiration catheter (105) to capture the clot; and engaging of the clot and the non-powered internal structural impediment (150, 150', 250, 350, 350', 450, 550, 650, 750, 850, 950, 1010, 1125) during resulting relative movement between the clot and the non-powered internal structural impediment (150, 150', 250, 350, 350', 450, 550, 650, 750, 850, 950, 1010, 1125) while subject to the cyclic aspiration pressure waveform.

Clause 12

The method of Clause 11, wherein the engaging step resulting in: (i) disrupting a structure of the clot from that of a single unitary mass into a plurality of clot pieces; (ii) altering a shape of at least a portion of the clot; and/or (iii) restricting distal movement of the clot.

Clause 13

The method of any of Clauses 11 through 12, wherein the relative movement is bi-directional movement.

Clause 14

The method of any of Clauses 11 through 13, wherein the non-powered internal structural impediment (150, 150', 250, 350, 350', 450, 550, 650, 750, 850, 950, 1010, 1125) projects into or spans at least a portion of the lumen of the aspiration catheter.

Clause 15

The method of any of Clauses 11 through 14, wherein the non-powered internal structural impediment (150, 150', 250, 350, 350', 450, 550) projects into the lumen of the aspiration catheter and is a wire, a fiber, a strut, a rib, teeth, blades, or spikes.

Clause 16

The method of any of Clauses 11 through 15, wherein the non-powered internal structural impediment (250, 350, 350') produces an aspiration vortex.

Clause 17

The method of any of Clauses 11 through 14, wherein the non-powered internal structural impediment is flaps (850) transitionable between an open state and a closed state in response to: (i) the cyclic aspiration pressure waveform; (ii) movement of the clot; and/or (iii) an ancillary device advanced in a distal direction through the lumen of the aspiration catheter (105).

Clause 18

The method of any of Clauses 11 through 14, wherein the non-powered internal structural impediment is a section (750) along the inner wall of the aspiration catheter (105) having a non-uniform contour.

Clause 19

The method of any of Clauses 11 through 18, further comprising a supplemental non-powered internal structural impediment as a section (605) of the aspiration catheter (105) axially compressible and expandable together with the clot capturable therein in response to the cyclic aspiration pressure waveform.

Clause 20

The method of any of Clauses 11 through 19, wherein the non-powered internal structural impediment (150, 150', 250, 350, 350', 450, 550, 650, 750, 850, 950, 1010, 1125) is: (i) permanently secured within the lumen of the aspiration catheter (105); or (ii) a separate component slidable therein the lumen of the aspiration catheter (105) and in the form of a shaft or wire having a plurality of cutting elements.

The descriptions contained herein are examples and are not intended in any way to limit the scope of the present disclosure. As described herein, the present disclosure contemplates many variations and modifications of the aspiration catheter including a non-powered internal structural impediment and cutting elements associated therewith assisting in capture of a clot when under cyclic aspiration. Modifications and variations apparent to those having skilled in the pertinent art according to the teachings of this disclosure are intended to be within the scope of the claims which follow.

What is claimed is:

1. A cyclic aspiration system comprising:

an aspiration catheter having a proximal end, an opposite distal end, respective outer and inner walls extending in a longitudinal direction from the proximal end to the distal end defining therein a lumen;

a cyclic aspiration source connected in fluid communication to the proximal end of the aspiration catheter; the cyclic aspiration pressure source producing a cyclic aspiration pressure waveform of intermittently cycling intervals of a vacuum pressure below atmospheric pressure and a positive pressure higher than the vacuum pressure; and a non-powered internal structural impediment disposed within the lumen of the aspiration catheter and configured to engage with a clot capturable therein during resulting movement between the clot and the non-powered internal structural impediment while subject to the cyclic aspiration pressure waveform, the non-powered internal structural impediment are flaps transitionable between an open state and a closed state.

2. The cyclic aspiration system in accordance with claim 1, wherein the engagement of the clot capturable therein with the non-powered internal structural impediment resulting in: (i) disrupting a structure of the clot capturable therein from that of a single unitary mass into a plurality of clot pieces; (ii) altering a shape of at least a portion of the clot capturable therein; and/or (iii) restricting distal movement of the clot capturable therein.

3. The cyclic aspiration system in accordance with claim 1, wherein movement between the clot and the non-powered internal structural impediment is bi-directional.

4. The cyclic aspiration system in accordance with claim 1, wherein the non-powered internal structural impediment projects into or spans at least a portion of the lumen of the aspiration catheter.

5. The cyclic aspiration system in accordance with claim 1, wherein the non-powered internal structural impediment is a wire, a fiber, a strut, a rib, teeth, blades, or spikes.

6. The cyclic aspiration system in accordance with claim 1, wherein the non-powered internal structural impediment is a section along the inner wall of the lumen of the aspiration catheter having a non-uniform contour.

7. The cyclic aspiration system in accordance with claim 1, further comprising a supplemental non-powered internal structural impediment as a section of the aspiration catheter axially compressible and expandable together with the clot capturable therein in response to the cyclic aspiration pressure waveform.

8. The cyclic aspiration system in accordance with claim 1, wherein the non- powered internal structural impediment is: (i) permanently secured within the lumen of the aspiration catheter; or (ii) a separate component slidable therein the lumen of the aspiration catheter and in the form of a shaft or wire having a plurality of cutting elements.

9. The cyclic aspiration system in accordance with claim 1, wherein the cyclic aspiration source is a pulsatile vacuum pump.

10. A method for using a cyclic aspiration system including:

an aspiration catheter having a proximal end, an opposite distal end, respective outer and inner walls extending in a longitudinal direction from the proximal end to the distal end defining therein a lumen; a cyclic aspiration source connected in fluid communication to the proximal end of the aspiration catheter; the cyclic aspiration pressure source producing a cyclic aspiration pressure waveform of intermittently cycling intervals of a vacuum pressure below atmospheric pressure and a positive pressure higher than the vacuum pressure; and a non-powered internal structural impediment disposed within the lumen of the aspiration catheter and configured to engage with a clot capturable therein during resulting movement between the clot and the internal structural impediment while subject to the cyclic aspiration pressure waveform, the non-powered internal structural impediment are flaps transitionable between an open state and a closed state in response to: (i) the cyclic aspiration pressure waveform; (ii) movement of the clot; and/or (iii) an ancillary device advanced in a distal direction through the lumen of the aspiration catheter; the method comprising the steps of:

either simultaneously or in series, advancing through a vessel to a target site on a proximal side of the clot the aspiration catheter and the non-powered internal structural impediment;

applying the cyclic aspiration pressure waveform to the aspiration catheter to capture the clot; and engaging of the clot and the non-powered internal structural impediment during resulting relative movement between the clot and the non-powered internal structural impediment while subject to the cyclic aspiration pressure waveform.

11. The method in accordance with claim 10, wherein the engaging step resulting in: (i) disrupting a structure of the clot from that of a single unitary mass into a plurality of clot pieces; (ii) altering a shape of at least a portion of the clot; and/or (iii) restricting distal movement of the clot.

12. The method in accordance with claim 10, wherein the relative movement is bi-directional movement.

13. The method in accordance with claim 10, wherein the non-powered internal structural impediment projects into or spans at least a portion of the lumen of the aspiration catheter.

14. The method in accordance with claim 10, wherein the non-powered internal structural impediment projects into the lumen of the aspiration catheter and is a wire, a fiber, a strut, a rib, teeth, blades, or spikes.

15. The method in accordance with claim 14, wherein the non-powered internal structural impediment produces an aspiration vortex.

16. The method in accordance with claim 10, wherein the non-powered internal structural impediment is a section along the inner wall of the aspiration catheter having a non-uniform contour.

17. The method in accordance with claim 10, further comprising a supplemental non-powered internal structural impediment as a section of the aspiration catheter axially compressible and expandable together with the clot capturable therein in response to the cyclic aspiration pressure waveform.

18. The method in accordance with claim 10, wherein the non-powered internal structural impediment is: (i) permanently secured within the lumen of the aspiration catheter; or (ii) a separate component slidable therein the lumen of the aspiration catheter and in the form of a shaft or wire having a plurality of cutting elements.

19. A cyclic aspiration system comprising:

an aspiration catheter having a proximal end, an opposite distal end, respective outer and inner walls extending in a longitudinal direction from the proximal end to the distal end defining therein a lumen;

a cyclic aspiration source connected in fluid communication to the proximal end of the aspiration catheter; the cyclic aspiration pressure source producing a cyclic aspiration pressure waveform of intermittently cycling intervals of a vacuum pressure below atmospheric pressure and a positive pressure higher than the vacuum pressure;

a non-powered internal structural impediment disposed within the lumen of the aspiration catheter and configured to engage with a clot capturable therein during resulting movement between the clot and the non-powered internal structural impediment while subject to the cyclic aspiration pressure waveform; and a supplemental non-powered internal structural impediment as a section of the aspiration catheter axially compressible and expandable together with the clot capturable therein in response to the cyclic aspiration pressure waveform.

20. A method for using a cyclic aspiration system including:

an aspiration catheter having a proximal end, an opposite distal end, respective outer and inner walls extending in a longitudinal direction from the proximal end to the distal end defining therein a lumen; a cyclic aspiration source connected in fluid communication to the proximal end of the aspiration catheter; the cyclic aspiration pressure source producing a cyclic aspiration pressure waveform of intermittently cycling intervals of a vacuum pressure below atmospheric pressure and a positive pressure higher than the vacuum pressure;

a non-powered internal structural impediment disposed within the lumen of the aspiration catheter and configured to engage with a clot capturable therein during resulting movement between the clot and the internal structural impediment while subject to the cyclic aspiration pressure waveform;

a supplemental non-powered internal structural impediment as a section of the aspiration catheter axially compressible and expandable together with the clot capturable therein in response to the cyclic aspiration pressure waveform; the method comprising the steps of:

either simultaneously or in series, advancing through a vessel to a target site on a proximal side of the clot the aspiration catheter and the non-powered internal structural impediment;

applying the cyclic aspiration pressure waveform to the aspiration catheter to capture the clot; and engaging of the clot and the non-powered internal structural impediment during resulting relative movement between the clot and the non-powered internal structural impediment while subject to the cyclic aspiration pressure waveform.

\* \* \* \* \*